(12) United States Patent
Taguchi et al.

(10) Patent No.: US 12,705,738 B2
(45) Date of Patent: Aug. 11, 2026

(54) METHOD OF GENERATING A TRAINED MODEL THAT TRANSFORMS FORWARD-PROJECTED X-RAY CT IMAGE DATA INTO RAW PROJECTION DATA

(71) Applicant: Canon Kabushiki Kaisha, Tokyo (JP)

(72) Inventors: Hiroki Taguchi, Otawara (JP); Yohei Minatoya, Bunkyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 349 days.

(21) Appl. No.: 18/499,281

(22) Filed: Nov. 1, 2023

(65) Prior Publication Data

US 2024/0070862 A1 Feb. 29, 2024

Related U.S. Application Data

(63) Continuation of application No. PCT/JP2022/044146, filed on Nov. 30, 2022.

(30) Foreign Application Priority Data

Nov. 30, 2021 (JP) ................................ 2021-194761

(51) Int. Cl.
*A61B 6/03* (2006.01)
*A61B 6/00* (2006.01)
(Continued)

(52) U.S. Cl.
CPC ............ *G06T 7/0012* (2013.01); *A61B 6/032* (2013.01); *A61B 6/461* (2013.01); *A61B 6/5205* (2013.01);
(Continued)

(58) Field of Classification Search
CPC ......... A61B 6/00; A61B 6/5205; A61B 6/032; G06T 7/10; G06T 2207/20081
See application file for complete search history.

(56) References Cited

U.S. PATENT DOCUMENTS 10,045,743 B2 * 8/2018 Grant ..................... A61B 6/032
2010/0128948 A1 5/2010 Thomsen et al.
(Continued)

FOREIGN PATENT DOCUMENTS

CN 106251383 A * 12/2016 ........... G06T 11/003
JP 2007-202700 A 8/2007
(Continued)

OTHER PUBLICATIONS

International Search Report issued Jan. 17, 2023 in PCT/JP2022/044146 filed on Nov. 30, 2022, 2 pages.
(Continued)

*Primary Examiner* — Siamak Harandi
(74) *Attorney, Agent, or Firm* — Oblon, McClelland, Maier & Neustadt, L.L.P.

(57) ABSTRACT

A medical information processing method according to an embodiment includes: acquiring an X-ray CT image (I1) and spectral information on imaging of the X-ray CT image (I1); acquiring sets of distribution data (D11, D12, and D13) on substances in the X-ray CT image by performing segmentation of the X-ray CT image (I1) according to substance; acquiring plural sets of forward projection data (P11, P12, and P13) on the respective substances by performing forward projection processes for the sets of distribution data (D11, D12, and D13) on the basis of the spectral information and attenuation coefficients for the respective substances; and generating a trained model (M1) by machine learning based on the plural sets of forward projection data (P11, P12, and P13) and raw data (R1) used in generation of the X-ray CT image (I1).

10 Claims, 14 Drawing Sheets

(51) Int. Cl.

| | |
|---|---|
| ***A61B 6/46*** | (2024.01) |
| ***G06T 7/00*** | (2017.01) |
| ***G06T 7/10*** | (2017.01) |

(52) U.S. Cl.

CPC ...... *G06T 7/10* (2017.01); *G06T 2207/10081* (2013.01); *G06T 2207/20081* (2013.01)

(56) References Cited

U.S. PATENT DOCUMENTS

| | | | |
|---|---|---|---|
| 2017/0278279 | A1 | 9/2017 | Krauss et al. |
| 2020/0234471 | A1 | 7/2020 | Lu et al. |
| 2020/0359987 | A1 | 11/2020 | Fan et al. |
| 2021/0007691 | A1 | 1/2021 | Prabhu Verleker et al. |
| 2021/0142480 | A1 | 5/2021 | Thomson et al. |
| 2021/0161487 | A1 | 6/2021 | Chen et al. |

FOREIGN PATENT DOCUMENTS

| | | | |
|---|---|---|---|
| JP | 2010-125332 | A | 6/2010 |
| JP | 2020-116377 | A | 8/2020 |
| JP | 2020-201244 | A | 12/2020 |
| JP | 2021-10727 | A | 2/2021 |
| JP | 2021-77331 | A | 5/2021 |

OTHER PUBLICATIONS

Office Action issued Mar. 31, 2026, in corresponding Chinese Patent Application No. 202280037249.2, with English Translation, 13 pages.

* cited by examiner

FIG.3

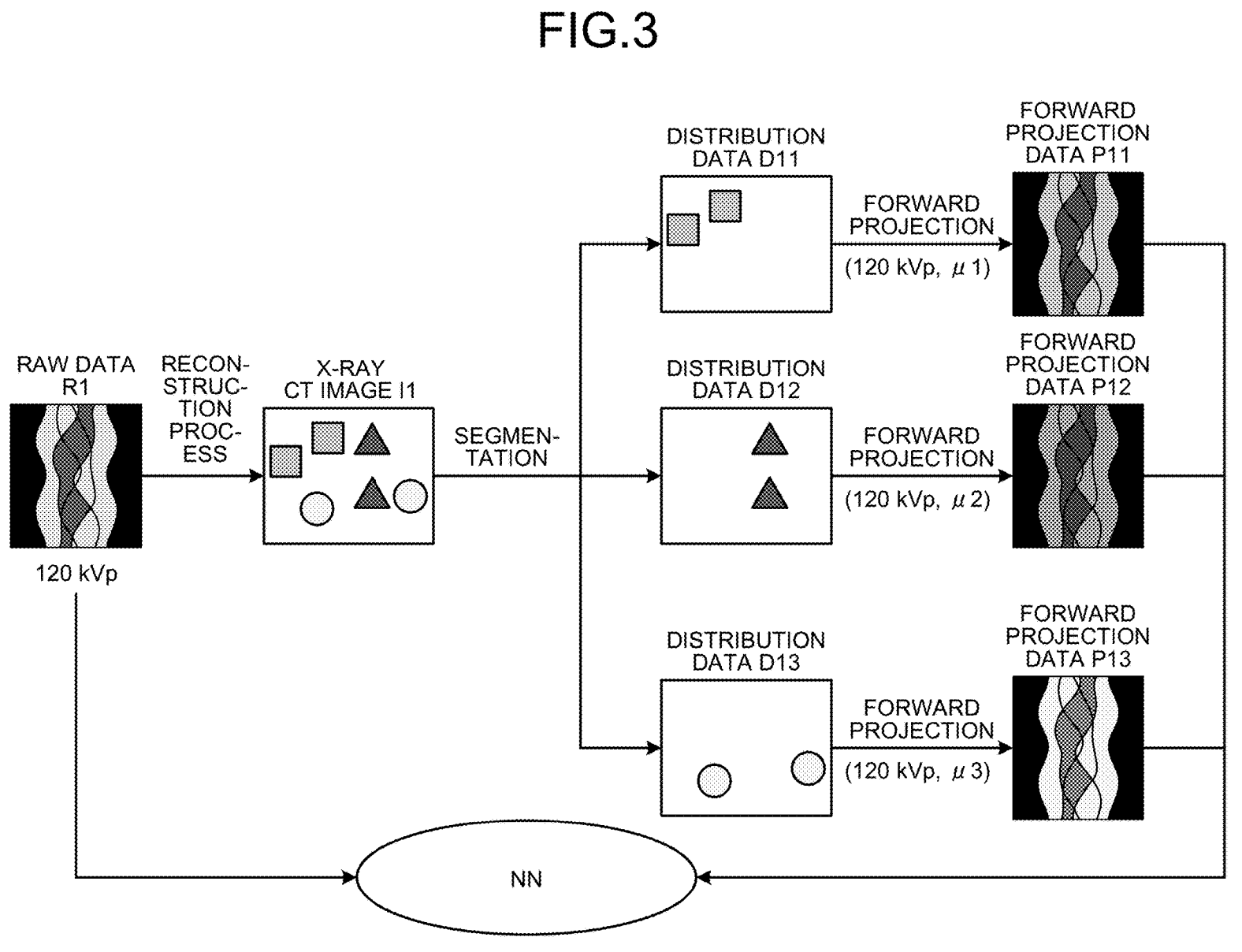

RAW DATA R1
120 kVp
RECON-STRUC-TION PROC-ESS
X-RAY CT IMAGE I1
SEGMEN-TATION
DISTRIBUTION DATA D11
DISTRIBUTION DATA D12
DISTRIBUTION DATA D13
FORWARD PROJECTION (120 kVp, $\mu$1)
FORWARD PROJECTION (120 kVp, $\mu$2)
FORWARD PROJECTION (120 kVp, $\mu$3)
FORWARD PROJECTION DATA P11
FORWARD PROJECTION DATA P12
FORWARD PROJECTION DATA P13
NN

FIG.4

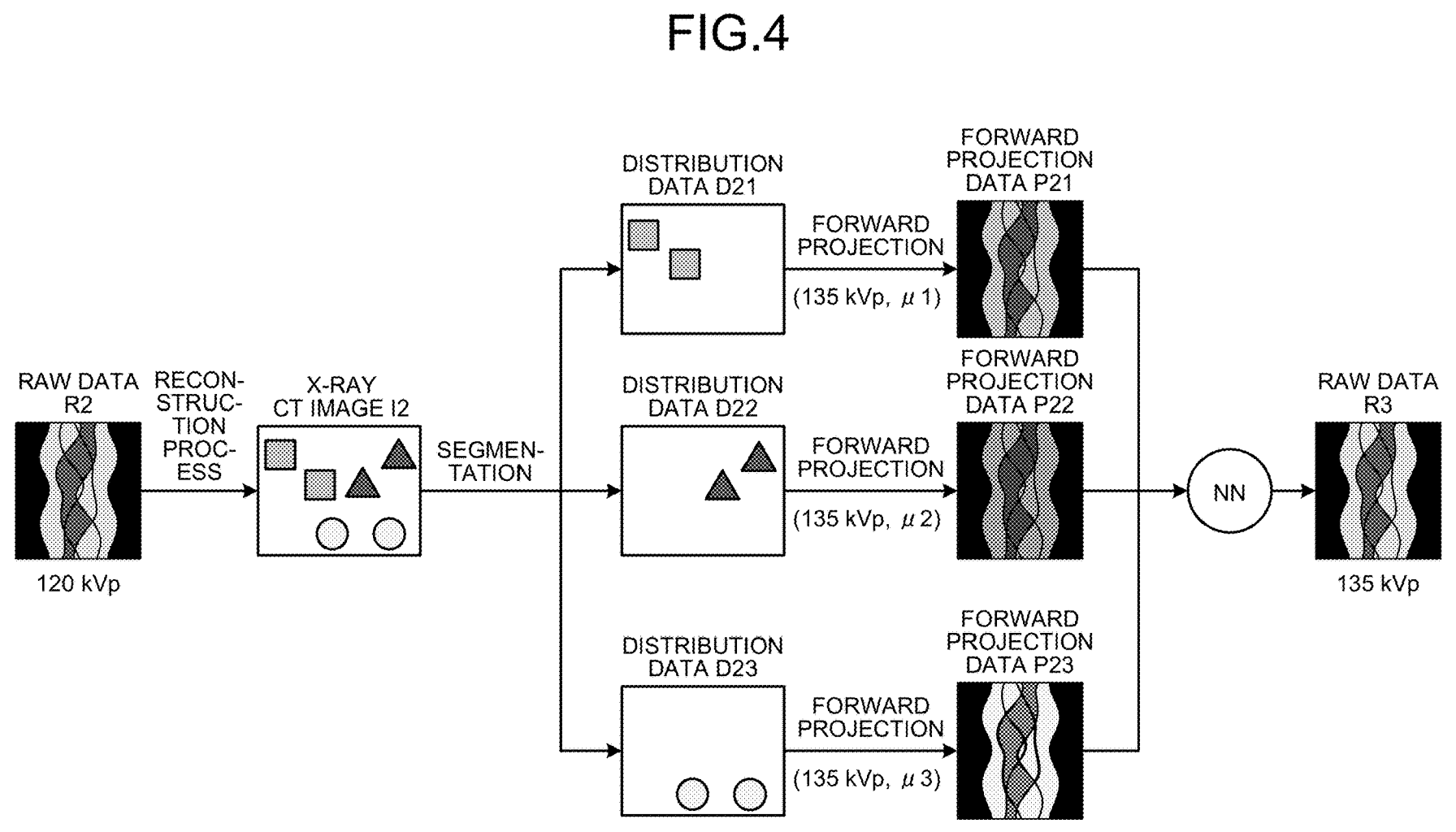

RAW DATA R2
120 kVp
RECON-STRUC-TION PROC-ESS
X-RAY CT IMAGE I2
SEGMEN-TATION
DISTRIBUTION DATA D21
DISTRIBUTION DATA D22
DISTRIBUTION DATA D23
FORWARD PROJECTION (135 kVp, $\mu$1)
FORWARD PROJECTION (135 kVp, $\mu$2)
FORWARD PROJECTION (135 kVp, $\mu$3)
FORWARD PROJECTION DATA P21
FORWARD PROJECTION DATA P22
FORWARD PROJECTION DATA P23
NN
RAW DATA R3
135 kVp

FIG.9

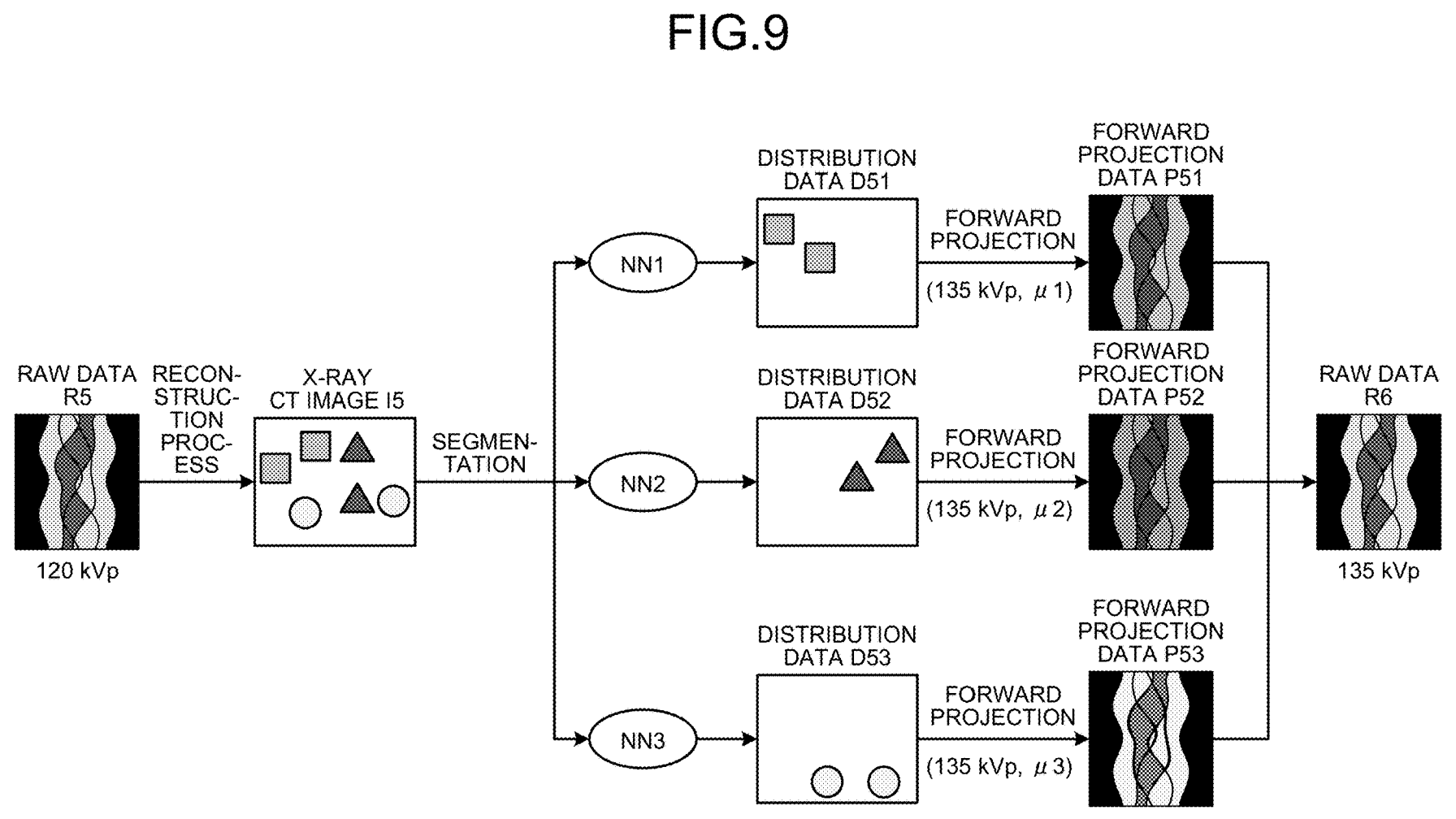

RAW DATA R5
120 kVp
RECON-STRUC-TION PROC-ESS
X-RAY CT IMAGE I5
SEGMEN-TATION
NN1
NN2
NN3
DISTRIBUTION DATA D51
DISTRIBUTION DATA D52
DISTRIBUTION DATA D53
FORWARD PROJECTION (135 kVp, $\mu$1)
FORWARD PROJECTION (135 kVp, $\mu$2)
FORWARD PROJECTION (135 kVp, $\mu$3)
FORWARD PROJECTION DATA P51
FORWARD PROJECTION DATA P52
FORWARD PROJECTION DATA P53
RAW DATA R6
135 kVp

FIG.12

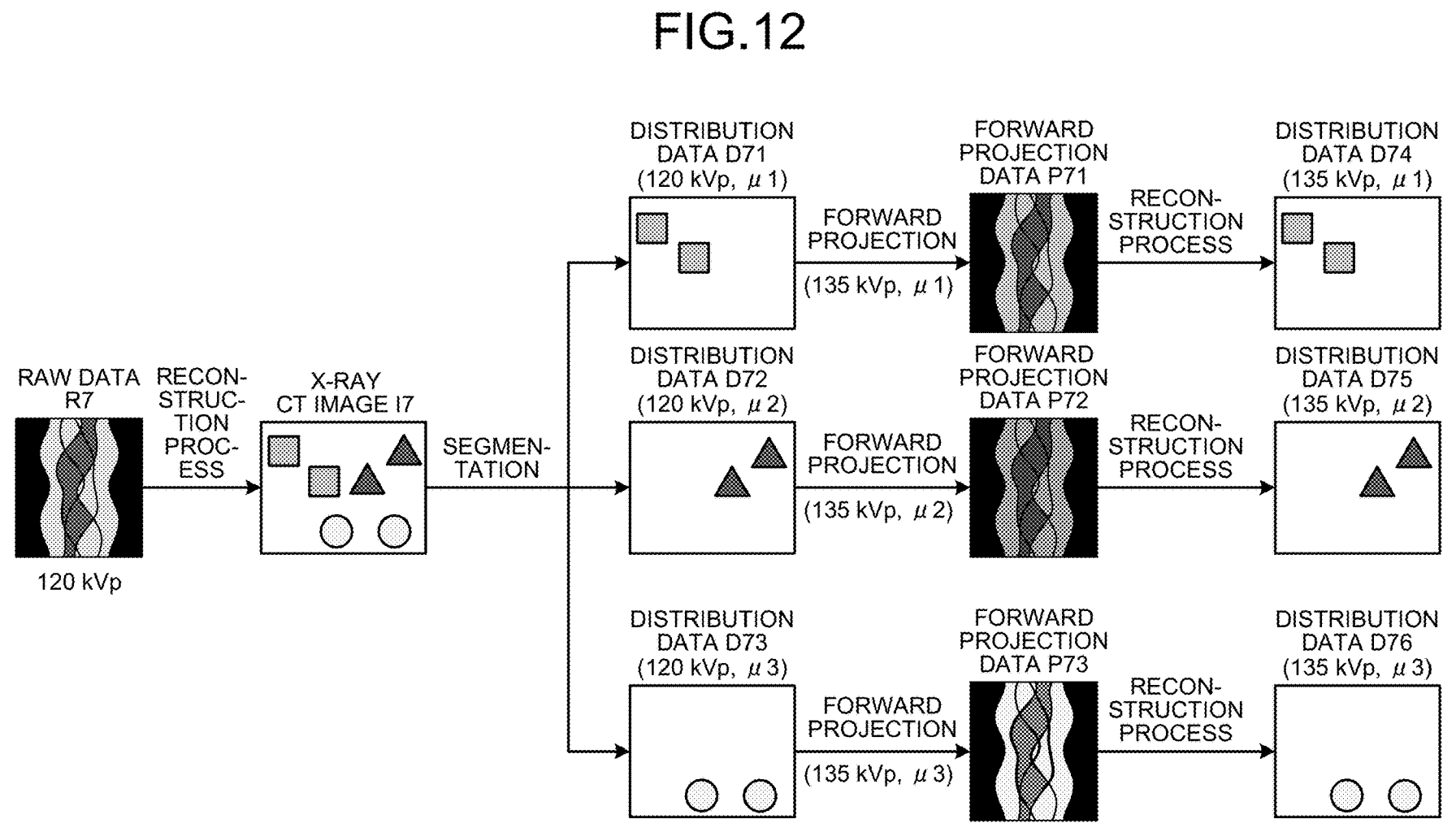

RAW DATA R7
120 kVp
RECON-STRUC-TION PROC-ESS
X-RAY CT IMAGE I7
SEGMEN-TATION
DISTRIBUTION DATA D71 (120 kVp, μ1)
DISTRIBUTION DATA D72 (120 kVp, μ2)
DISTRIBUTION DATA D73 (120 kVp, μ3)
FORWARD PROJECTION (135 kVp, μ1)
FORWARD PROJECTION (135 kVp, μ2)
FORWARD PROJECTION (135 kVp, μ3)
FORWARD PROJECTION DATA P71
FORWARD PROJECTION DATA P72
FORWARD PROJECTION DATA P73
RECON-STRUCTION PROCESS
RECON-STRUCTION PROCESS
RECON-STRUCTION PROCESS
DISTRIBUTION DATA D74 (135 kVp, μ1)
DISTRIBUTION DATA D75 (135 kVp, μ2)
DISTRIBUTION DATA D76 (135 kVp, μ3)

FIG.13

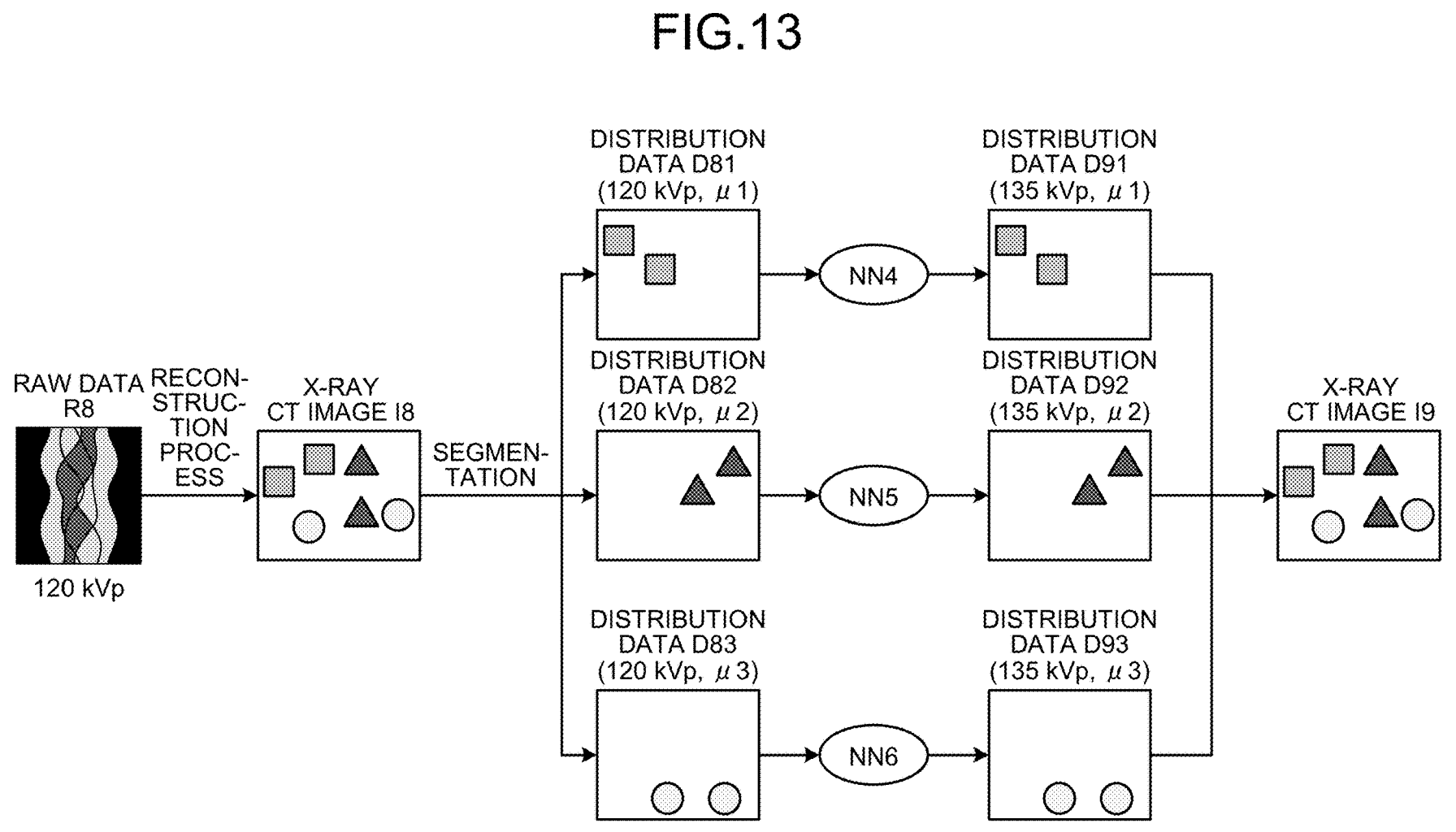

RAW DATA R8
120 kVp
RECON-STRUC-TION PROC-ESS
X-RAY CT IMAGE I8
SEGMEN-TATION
DISTRIBUTION DATA D81 (120 kVp, μ1)
DISTRIBUTION DATA D82 (120 kVp, μ2)
DISTRIBUTION DATA D83 (120 kVp, μ3)
NN4
NN5
NN6
DISTRIBUTION DATA D91 (135 kVp, μ1)
DISTRIBUTION DATA D92 (135 kVp, μ2)
DISTRIBUTION DATA D93 (135 kVp, μ3)
X-RAY CT IMAGE I9

START
S411
ACQUIRE RAW DATA
S412
RECONSTRUCTION
S413
SEGMENTATION
S414
FORWARD PROJECTION
S415
RECONSTRUCTION
S416
ASSOCIATE DISTRIBUTION DATA OBTAINED THROUGH S413 WITH DISTRIBUTION DATA OBTAINED THROUGH S415 TO FORM ONE SET OF TRAINING DATA
END

START
S421
ACQUIRE PLURAL SETS OF TRAINING DATA THROUGH S416
S422
GENERATE TRAINED MODEL M3 FOR EACH kVp COMBINATION
END

METHOD OF GENERATING A TRAINED MODEL THAT TRANSFORMS FORWARD-PROJECTED X-RAY CT IMAGE DATA INTO RAW PROJECTION DATA

CROSS-REFERENCE TO RELATED APPLICATIONS

This application is a continuation of PCT international application Ser. No. PCT/JP2022/044146 filed on Nov. 30, 2022 which designates the United States, incorporated herein by reference, and which claims the benefit of priority from Japanese Patent Application No. 2021-194761, filed on Nov. 30, 2021, the entire contents of which are incorporated herein by reference.

FIELD

Embodiments disclosed in this specification and the drawings relate to medical information processing methods and medical information processing apparatuses.

BACKGROUND

X-ray computed tomography (CT) images are widely used in clinical settings. Imaging conditions for X-ray CT images are adjusted as appropriate according to purpose of X-ray interpretation.

For example, an X-ray spectrum to be used for X-ray interpretation may be set as an imaging condition for an X-ray CT image. For example, in capturing an X-ray CT image, the X-ray CT image is able to be acquired by irradiating a subject with X-rays having a spectrum corresponding to a set X-ray energy value and reconstructing projection data based on an X-ray detection result.

A user, for example, a medical doctor, may want to refer to an X-ray CT image acquired in another X-ray spectrum after an X-ray CT image has been acquired. For example, the user may determine that an image with greater contrast or an image with less noise is preferably referred to for the purpose of making a diagnosis of a subject's condition. However, acquiring another X-ray CT image in another X-ray spectrum again increases the subject's radiation exposure.

Patent Literature 1: Japanese Unexamined Patent Application Publication No. 2021-10727

Patent Literature 2: Japanese Unexamined Patent Application Publication No. 2007-202700

Patent Literature 3: Japanese Unexamined Patent Application Publication No. 2020-201244

One of problems to be solved by embodiments disclosed in the specification and the drawings is to enable acquisition of an X-ray CT image corresponding to spectral information on X-rays, the spectral information being different from that on X-rays used at the time of imaging. However, the problems to be solved by the embodiments disclosed in the specification and the drawings are not limited to the above mentioned problem. Any problems corresponding to effects provided by configurations disclosed through the embodiments described later may be regarded as alternative objects.

BRIEF DESCRIPTION OF THE DRAWINGS

FIG. 3 is a diagram for explanation of a learning phase according to the first embodiment;

FIG. 4 is a diagram for explanation of an application phase according to the first embodiment;

FIG. 9 is a diagram for explanation of an application phase according to the third embodiment;

FIG. 12 is a diagram illustrating an example of a method of acquiring training data according to the fourth embodiment;

FIG. 13 is a diagram for explanation of an application phase according to the fourth embodiment;

DETAILED DESCRIPTION

Figure 1:
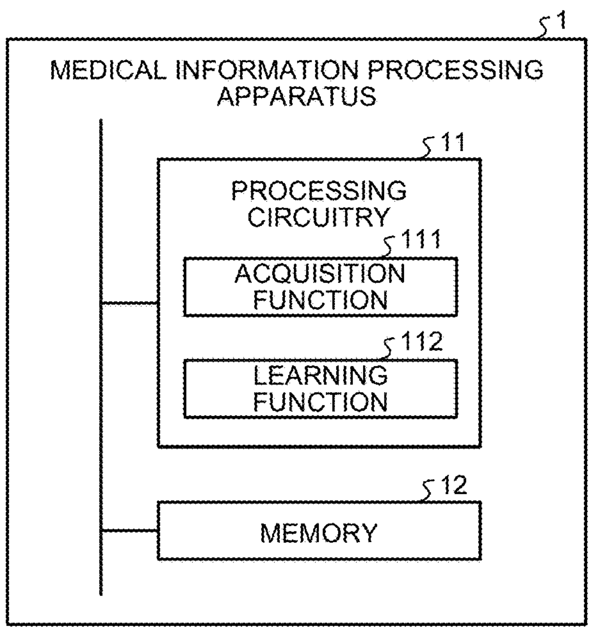
FIG. 1 is a block diagram illustrating an example of a configuration of a medical information processing apparatus according to a first embodiment.

A medical information processing method includes acquiring an X-ray CT image and spectral information on imaging of the X-ray CT image, performing segmentation of the X-ray CT image according to substance and acquiring distribution data on substances in the X-ray CT image, performing a forward projection process for the distribution data on the basis of the spectral information and an attenuation coefficient for each substance, and acquiring plural sets of forward projection data respectively for the substances; and generating a trained model by machine learning based on the plural sets of forward projection data and raw data used in generation of the X-ray CT image.

Embodiments of the medical information processing method and a medical information processing apparatus will hereinafter be described in detail while reference if made to the appended drawings.

First Embodiment

A medical information processing apparatus 1 illustrated in FIG. 1 will be described first. The medical information processing apparatus 1 generates a trained model M1 described later and thereby enables acquisition of an X-ray CT image corresponding to spectral information on X-rays, the spectral information being different from that on X-rays used at the time of imaging. In other words, the medical information processing apparatus 1 generates the trained model M1 for a conversion process to other X-ray energy (kVp). The medical information processing apparatus 1 includes, for example, processing circuitry 11 and a memory 12.

The processing circuitry 11 implements an acquisition function 111 and a learning function 112 and thereby controls the overall operation of the medical information processing apparatus 1. The acquisition function 111 is an example of an acquisition unit. The learning function 112 is an example of a learning unit.

For example, the processing circuitry 11 reads and executes a program corresponding to the acquisition function 111 from the memory 12 and thereby acquires various training data described later. Furthermore, the processing circuitry 11 reads and executes a program corresponding to the learning function 112 from the memory 12 and thereby executes machine learning using the training data acquired by the acquisition function 111 and generates the trained model M1. Details of processing performed by the acquisition function 111 and the learning function 112 will be described later.

Processing functions in the form of programs executable by a computer have been stored in the memory 12 of the medical information processing apparatus 1 illustrated in FIG. 1. The processing circuitry 11 is a processor that implements the functions corresponding to the programs by reading and executing the programs from the memory 12. In other words, the processing circuitry 11 that has read the programs has the functions corresponding to the read programs.

The acquisition function 111 and the learning function 112 have been described to be implemented by the single piece of processing circuitry 11 in FIG. 1, but the processing circuitry 11 may include a combination of plural independent processors and the functions may be implemented by these processors executing the programs. Furthermore, any of the processing functions of the processing circuitry 11 may be implemented by being distributed to plural pieces of processing circuitry or integrated into a single piece of processing circuitry, as appropriate.

The memory 12 is implemented by, for example: a semiconductor memory element, such as a random access memory (RAM) or a flash memory; a hard disk; or an optical disk. For example, the memory 12 stores programs for the circuitry included in the medical information processing apparatus 1 to implement functions of the circuitry. The memory 12 also stores the various training data described later.

A medical information processing system illustrated in FIG. 2 will be described next. The medical information processing system includes, for example, an X-ray CT apparatus 2 and a medical information processing apparatus 3. By using an X-ray CT image captured by the X-ray CT apparatus 2 and the trained model M1 generated by the medical information processing apparatus 1, the medical information processing apparatus 3 acquires an X-ray CT image corresponding to spectral information on X-rays, the spectral information being different from that on X-rays used at the time of imaging by the X-ray CT apparatus 2.

The X-ray CT apparatus 2 includes, for example, an X-ray tube and an X-ray detector at opposite positions between which a subject is to be interposed. The X-ray CT apparatus 2 detects, by means of the X-ray detector, X-rays emitted from the X-ray tube and transmitted through the subject and thereby acquires projection data (raw data). The X-ray CT apparatus 2 is also capable of performing a reconstruction process for projection data acquired for each X-ray irradiation angle (view) to acquire an X-ray CT image.

The medical information processing apparatus 3 includes, for example, a memory 31, a display 32, an input interface 33, and processing circuitry 34.

The memory 31 is implemented by, for example: a semiconductor memory element, such as a random access memory (RAM) or a flash memory; a hard disk; or an optical disk. For example, the memory 31 stores programs for the circuitry included in the medical information processing apparatus 3 to implement functions of the circuitry. The memory 31 also stores the trained model M1 generated by the medical information processing apparatus 1.

The display 32 displays various kinds of information. For example, the display 32 displays various X-ray CT images. The display 32 also displays a graphical user interface (GUI) for receiving, for example, various instructions and settings from a user via the input interface 33. For example, the display 32 is a liquid crystal display or a cathode ray tube (CRT) display. The display 32 may be a desktop display, or may be a tablet terminal that enables wireless communication with the medical information processing apparatus 3.

The input interface 33 receives various input operations from a user, converts the input operations received, into electric signals, and outputs the electric signals to the processing circuitry 34. For example, the input interface 33 is implemented by any of: a mouse and a keyboard; a trackball; switches; buttons; a joystick; a touchpad enabling an input operation by a touch on an operation surface; a touch screen having a display screen and a touchpad that have been integrated together; a non-contact input circuit using an optical sensor; and a voice input circuit. The input interface 33 may be a tablet terminal that enables wireless communication with the medical information processing apparatus 3, for example. Furthermore, the input interface 33 may be a circuit that receives an input operation from a user by motion capturing. For example, by processing signals acquired via a tracker or images collected with respect to a user, the input interface 33 may receive a body motion or line of sight of the user as an input operation. The input interface 33 does not necessarily include physical operation parts, such as a mouse and a keyboard. Examples of the input interface 33 also include an electric signal processing circuit that receives an electric signal corresponding to an operation input from an external input device provided separately from the medical information processing apparatus 3 and outputs this electric signal to the processing circuitry 34.

The processing circuitry 34 implements an acquisition function 341, an image processing function 342, and a display control function 343 to thereby control the overall operation of the medical information processing apparatus 3.

For example, the processing circuitry 34 reads and executes a program corresponding to the acquisition function 341 from the memory 31 and thereby acquires plural sets of forward projection data described later. Furthermore, the processing circuitry 34 reads and executes a program corresponding to the image processing function 342 from the memory 31, and thereby inputs the plural sets of forward projection data acquired by the acquisition function 341 and acquires data corresponding to optional spectral information. The processing circuitry 34 also reads and executes a program corresponding to the display control function 343 from the memory 31 and thereby displays an X-ray CT image based on the data acquired by the image processing function 342, on the display 32. Details of processing by the acquisition function 341, the image processing function 342, and the display control function 343 will be described later.

Figure 2:
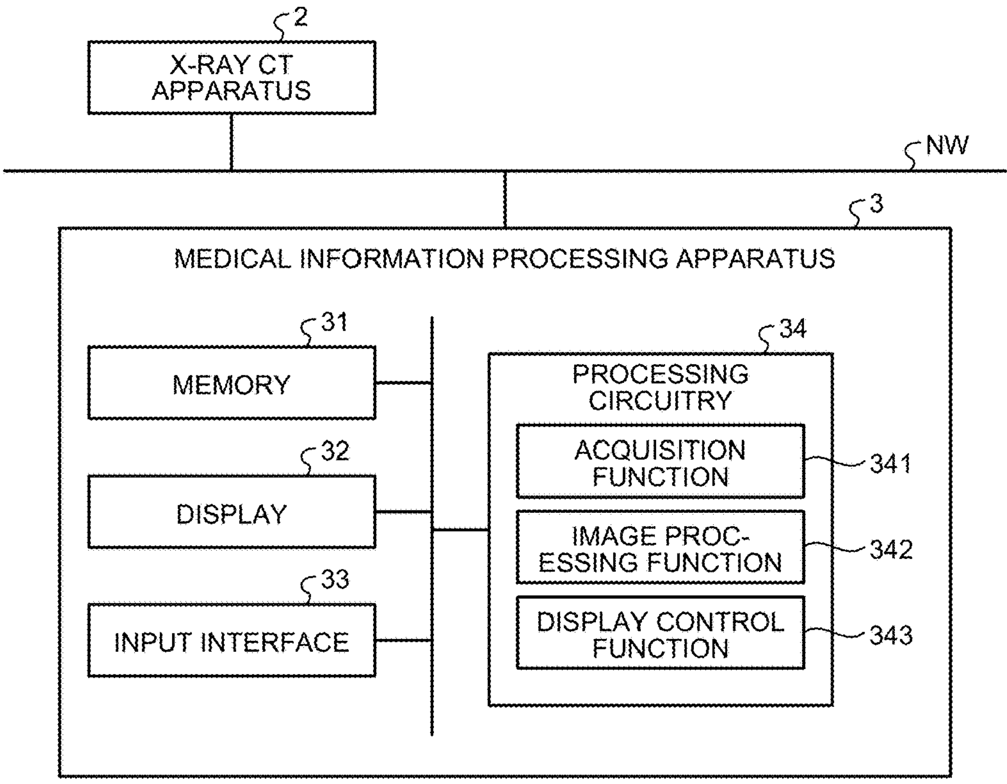
FIG. 2 is a block diagram illustrating an example of a configuration of a medical information processing system according to the first embodiment.

The processing functions in the form of programs executable by a computer have been stored in the memory 31 of the medical information processing apparatus 3 illustrated in FIG. 2. The processing circuitry 34 is a processor that implements the functions corresponding to the programs by reading and executing the programs from the memory 31. In other words, the processing circuitry 34 that has read the programs has the functions corresponding to the read programs.

The acquisition function 341, the image processing function 342, and the display control function 343 have been described to be implemented by the single piece of processing circuitry 34 in FIG. 2, but the processing circuitry 34 may include a combination of plural independent processers and the functions may be implemented by the processors executing the programs. Furthermore, any of the processing functions of the processing circuitry 34 may be implemented by being distributed to plural pieces of processing circuitry or integrated into a single piece of processing circuitry, as appropriate.

As illustrated in FIG. 2, the X-ray CT apparatus 2 and the medical information processing apparatus 3 are connected to each other via a network NW. The network NW may be a local network closed within an institution or may be a network via the Internet. Furthermore, communication between the X-ray CT apparatus 2 and the medical information processing apparatus 3 may be performed via another device, such as an image archiving device, or may be directly performed without another device. Examples of such an image archiving device include a server of a picture archiving and communication system (PACS).

The medical information processing apparatus 1, and the medical information processing system including the medical information processing apparatus 3 have been described above. The medical information processing apparatus 1 configured as described above generates the trained model M1 and thereby enables acquisition of an X-ray CT image at the medical information processing apparatus 3, the X-ray CT image corresponding to optional X-ray spectral information different from spectral information on X-rays used at the time of imaging.

A process in which the trained model M1 is generated by the medical information processing apparatus 1 will be described by use of FIG. 3. FIG. 3 is a diagram for explanation of a learning phase according to the first embodiment.

Firstly, imaging of any subject is executed and raw data R1 are collected. The raw data R1 are, for example, a sinogram. The raw data R1 may be collected by the X-ray CT apparatus 2 illustrated in FIG. 2 or may be collected by another X-ray CT apparatus. Subsequently, a reconstruction process based on the raw data R1 is executed and an X-ray CT image I1 is generated. The acquisition function 111 acquires the X-ray CT image I1.

The reconstruction process for the X-ray CT image I1 may be performed by the acquisition function 111 or may be performed at another device. For example, the X-ray CT apparatus 2 captures an image of a subject to collect the raw data R1, reconstructs the X-ray CT image I1 from the raw data R1 collected, and the acquisition function 111 acquires the X-ray CT image I1 reconstructed by the X-ray CT apparatus 2. Or, the X-ray CT apparatus 2 captures an image of a subject to collect the raw data R1 and the acquisition function 111 reconstructs the X-ray CT image I1 from the raw data R1 collected by the X-ray CT apparatus 2.

A method of reconstructing the X-ray CT image I1 is not particularly limited, but may be, for example, a filtered back projection (FBP) method, a successive approximation reconstruction method, or a successive approximation applied reconstruction method. Or, the X-ray CT image I1 may be reconstructed by a machine learning method. For example, the X-ray CT image I1 may be reconstructed by a deep learning reconstruction (DLR) method.

Subsequently, the acquisition function 111 performs segmentation of the acquired X-ray CT image I1 according to substance and acquires distribution data on substances in the X-ray CT image I1. For example, the acquisition function 111 performs segmentation of the X-ray CT image I1 into different organs.

A method for this segmentation is not particularly limited, but examples of the method include Otsu's Binarization Method based on CT values, a region growing method, the snakes method, the graph cuts method, and the mean shift method. Or, manual segmentation may be performed by displaying the X-ray CT image I1 and receiving an operation for specifying ranges of organs from a user.

Or, the acquisition function 111 may perform segmentation of the X-ray CT image I1 by a machine learning method. For example, performing machine learning with input data that are any X-ray CT images and output data that are results of manual segmentation of the X-ray CT images by a medical doctor enables generation of a trained model having a function of performing segmentation of an input X-ray CT image. By inputting the X-ray CT image I1 to such a trained model, the acquisition function 111 is able to acquire distribution data on substances in the X-ray CT image I1.

FIG. 3 illustrates a case where three sets of distribution data (distribution data D11, distribution data D12, and distribution data D13) are acquired by segmentation of the X-ray CT image I1 according to substance. However, FIG. 3 is just an example, and any number of sets of distribution data may be acquired by the segmentation.

Furthermore, the acquisition function 111 acquires spectral information on the imaging of the X-ray CT image I1. For example, the acquisition function 111 acquires spectral information on X-rays that were emitted from the X-ray tube of the X-ray CT apparatus 2 when the X-ray CT image I1 was captured. The spectral information is, for example, information having X-ray intensity associated with each wavelength (X-ray energy). The spectral information may be added as supplementary information to the X-ray CT image I1.

More specifically, the spectral information may be determined for each X-ray tube, according to a setting of X-ray energy used at the time of imaging of the X-ray CT image I1. For example, in a case where "120 kVp" has been set for X-ray energy, X-rays having a spectral range of "120 kVp" or less are emitted.

Furthermore, because different X-ray tubes have individual differences between their spectral forms, performing calibration of the X-ray tubes beforehand enables more accurate determination of spectral information. Such calibration may be executed using, for example, a spectroscopic detector. That is, measuring an X-ray spectrum using a spectroscopic detector for each X-ray tube and each setting of X-ray energy enables more accurate determination of spectral information on the imaging of the X-ray CT image I1. Such a spectroscopic detector to be used may be, for example, a detector using high-purity germanium.

The acquisition function 111 may acquire various kinds of data, such as X-ray CT images and spectral information, via the network NW or via a storage medium. Furthermore, the acquisition function 111 stores the data acquired, into the memory 12.

Subsequently, on the basis of the spectral information on the imaging of the X-ray CT image I1 and attenuation coefficients for respective substances, the acquisition function 111 performs forward projection processes for distribution data on the substances in the X-ray CT image I1 to acquire plural sets of forward projection data on the respective substances. For example, in a case illustrated in FIG. 3, the acquisition function 111 performs a forward projection process for the distribution data D11 to acquire forward projection data P11, performs a forward projection process for the distribution data D12 to acquire forward projection data P12, and performs a forward projection process for the distribution data D13 to acquire forward projection data P13.

That is, when forward projection is performed from a specific direction, distribution data on each substance in the X-ray CT image I1 indicate the length over which the substance is distributed on the path of the forward projection. That is, on the basis of distribution data on each substance in the X-ray CT image I1, a path length of the substance is able to be found. Using the path length and attenuation coefficient for each substance enables the absorbed X-ray dose to be found and forward projection data to be generated. A value disclosed in literature by, for example, National Institute of Standards and Technology (NIST) may be used as the attenuation coefficient for each substance.

More specifically, the distribution data are generated by a segmentation process and are presumed to correspond to a single substance, and a single attenuation coefficient is thus assigned to each set of distribution data. For example, an attenuation coefficient μ1 is assigned to the distribution data D11, an attenuation coefficient μ2 is assigned to the distribution data D12, and an attenuation coefficient μ3 is assigned to the distribution data D13. However, attenuation coefficients are dependent on X-ray energy and multicolor X-rays having a spectral range are emitted from the X-ray tube. Therefore, the acquisition function 111 is able to acquire forward projection data by integrating the attenuation coefficient μ1 as a function of X-ray energy and multiplying the integrated result by the path length.

Subsequently, the learning function 112 executes machine learning using training data that are various data acquired by the acquisition function 111. Specifically, the learning function 112 generates the trained model M1 for a conversion process for other X-ray energy (kVp) by machine learning based on the plural sets of forward projection data illustrated in FIG. 3 and the raw data R1 used in generation of the X-ray CT image I1.

Description will be made on the assumption that the trained model M1 is a neural network (NN) in FIG. 3. The neural network is a network having a structure with layers, adjacent ones of the layers being connected to each other, and information is propagated from an input layer to an output layer of the layers in the network. The neural network includes, for example, the input layer, plural intermediate layers (hidden layers), and the output layer.

For example, the learning function 112 inputs input data that are the plural sets of forward projection data acquired by the acquisition function 111 on the basis of the X-ray CT image I1, into the neural network. Furthermore, the learning function 112 inputs output data that are the raw data R1 used in reconstruction of the X-ray CT image I1, into the neural network. That is, the learning function 112 inputs, as correct answer data, the raw data R1 actually collected at the time of imaging of the X-ray CT image I1, into the neural network.

The plural sets of forward projection data input as the input data result from a forward projection process of each of sets of distribution data segmented according to substance, the forward projection process being based on spectral information and the attenuation coefficient for each of the substances. The sum of the plural sets of forward projection data is, similarly to the original raw data R1, data including information on the plural substances. However, there may be an error between the sum of the plural sets of forward projection data and the raw data R1. For example, the attenuation coefficients for the respective substances used in generating the forward projection data have been described above to be specific values (such as values disclosed in literature), but the attenuation coefficients for the substances may have individual differences among different subjects. Furthermore, in a case where a specific value is used as an attenuation coefficient for a liver of a subject, the value of the attenuation coefficient may vary depending on the position in the liver. In addition, errors attributable to the accuracy of the segmentation are also generated.

The learning function 112 generates the trained model M1 by causing the neural network to learn so that the error between the sum of the plural sets of forward projection data input as the input data and the raw data R1 input as the output data is minimized. For example, a relation between the sum of the plural sets of forward projection data and the raw data R1 is able to be expressed by Equation (1) below. This Equation (1) is able to be provided for each point on the sinogram. That is, Equation (1) is able to be provided for each ray (projection position and projection angle) of the forward projection.

$$\int\mu1(E)de*L1*c1+\int\mu2(E)dE*L2*c2+\int\mu3(E)dE*L3*c3=(\text{RawData}) \quad (1)$$

In Equation (1), (RawData) on the right side represents a pixel value at one point in the raw data R1. Furthermore, "∫μ1(E)dE*L1'" on the left side represents a pixel value at one point corresponding to (RawData) on the right side, the one point being among the forward projection data P11. In addition, "∫μ2(E)dE*L2'" on the left side represents a pixel value at one point corresponding to (RawData) on the right side, the one point being among the forward projection data P12. Furthermore, "∫μ3(E)dE*L3'" on the left side represents a pixel value at one point corresponding to (RawData) on the right side, the one point being among the forward projection data P13.

More specifically, "μ1" is an attenuation coefficient of a single substance corresponding to the forward projection data P11, "μ2" is an attenuation coefficient of a single substance corresponding to the forward projection data P12, and "μ3" is an attenuation coefficient of a single substance corresponding to the forward projection data P13. As described above, these attenuation coefficients are integrated as functions of X-ray energy, "E".

Furthermore, "L1'" is a path length acquired in forward projection using the distribution data D11 assumed to be for a single substance. That is, "L1'" is a known value based on the distribution data D11. Similarly, "L2'" is a path length acquired in forward projection using the distribution data D12 assumed to be for a single substance, and "L3'" is a path length acquired in forward projection using the distribution data D13 assumed to be for a single substance.

Furthermore, "c1", "c2", and "c3" are coefficients by which each term is multiplied for the equality in Equation (1) to be true. That is, as described above, an error attributable to the setting of the attenuation coefficient and the segmentation process, for example, is generated between the sum of the plural sets of forward projection data and the raw data R1. In Equation (1), the error is absorbed for the equality to be true by multiplications by coefficients, such as "c1", "c2", and "c3". In other words, in Equation (1), virtual path lengths "L1", "L2", and "L3" for Equation (2) to hold true are rewritten respectively by "L1'*c1", "L2'*c2", and "L3'*c3".

$$\int\mu 1(E)dE*L1+\int\mu 2(E)de*L2+\int\mu 3(E)de*L3=(\text{RawData}) \quad (2)$$

Therefore, in a case where the neural network is caused to learn with input data that are three terms on the left side of Equation (1), "∫μ1(E)dE*L1", "∫μ2(E)dE*L2'", and "∫μ3(E)dE*L3'", and output data that are (RawData) on the right side of Equation (1), for example, the neural network is able to learn coefficients like "c1", "c2", and "c3". Equation (1) may be provided multiply for respective points on the sinogram. Coefficients, such as "c1", "c2", and "c3", are usually not able to be solved as uniquely determined solutions and the neural network thus learns the coefficients so as to minimize the error between the left side and the right side in each of multiple Equations (1).

By executing the above described machine learning, the learning function 112 is able to generate the trained model M1 having learnt the coefficients, "c1", "c2", and "c3". That is, the learning function 112 generates the trained model M1 by causing the neural network to learn coefficients by which the plural sets of forward projection data are to be multiplied so that the error between the sum of the plural sets of forward projection data and the raw data R1 is minimized. The process of generating the trained model M1 by means of the learning function 112 is able to be executed offline.

The case where the error is absorbed by multiplication of the terms, "∫μ1(E)dE*L1", "∫μ2(E)dE*L2'", and "∫μ3(E)dE*L3'", by the coefficients, "c1", "c2", and "c3", in Equation (1) has been described. However, this embodiment is not limited to this case. That is, mathematics for absorption of the error are not limited to multiplication by coefficients.

For example, instead of multiplying each set of forward projection data by a coefficient as indicated on the left side of Equation (1), indices may be set or additional terms may be added. Any such mathematics or any combination thereof enables absorption of the error between the sum of plural sets of forward projection data and the raw data R1. In this case, the neural network will learn the mathematics or combination thereof for minimizing the error.

An application phase of the trained model M1 will be described next by use of FIG. 4. Firstly, imaging of any subject is executed and raw data R2 are collected. The raw data R2 may be collected from the same subject as the raw data R1 or may be collected from another subject. Furthermore, the raw data R2 may be collected by the X-ray CT apparatus 2 illustrated in FIG. 2 or may be collected by another X-ray CT apparatus. Subsequently, a reconstruction process based on the raw data R2 is executed and an X-ray CT image I2 is generated. The acquisition function 341 acquires the X-ray CT image I2.

The reconstruction of the X-ray CT image I2 may be performed by the acquisition function 341 or may be performed at another device. For example, the X-ray CT apparatus 2 captures an image of a subject to collect projection data and reconstructs the X-ray CT image I2 from the projection data collected, and the acquisition function 341 acquires the X-ray CT image I2 reconstructed by the X-ray CT apparatus 2. Alternatively, the X-ray CT apparatus 2 may capture an image of a subject to collect projection data, and the acquisition function 341 may reconstruct the X-ray CT image I2 from the projection data collected by the X-ray CT apparatus 2. A method of reconstructing the X-ray CT image I2 is not particularly limited.

Subsequently, the acquisition function 341 performs segmentation of the acquired X-ray CT image I2 according to substance and acquires distribution data on substances in the X-ray CT image I2. For example, the acquisition function 341 performs segmentation of the X-ray CT image I2 into different organs. A method for the segmentation is not particularly limited, and the segmentation may be performed by a machine learning method. FIG. 4 illustrates a case where three sets of distribution data (distribution data D21, distribution data D22, and distribution data D23) are acquired by segmentation of the X-ray CT image I2 according to substance.

Furthermore, on the basis of optional spectral information and attenuation coefficients for the respective substances, the acquisition function 341 performs a forward projection process for the sets of distribution data on the substances in the X-ray CT image I2 and acquires plural sets of forward projection data for the respective substances. For example, in the case illustrated in FIG. 4, the acquisition function 341 performs a forward projection process for the distribution data D21 to acquire forward projection data P21, performs a forward projection process for the distribution data D22 to acquire forward projection data P22, and performs a forward projection process for the distribution data D23 to acquire forward projection data P23.

The optional spectral information may be different from the spectral information on the imaging of the X-ray CT image 12. For example, in FIG. 4, the X-ray CT image I2 is captured using X-rays of "120 kVp". By contrast, the optional spectral information set for acquisition of the forward projection data is "135 kVp".

The optional spectral information may be set on the basis of, for example, an X-ray energy value input by a user. For example, a user operates a GUI displayed on the display 32 to input a desired X-ray energy value. For example, in a case where the imaging condition for the X-ray CT image I2 is "120 kVp" and an image higher in contrast than the X-ray CT image I2 is desired to be referred to, a user may input an X-ray energy value lower than "120 kVp". Alternatively, in a case where an image having less noise than the X-ray CT image 12 is desired to be referred to, the user may input an X-ray energy value higher than "120 kVp".

By inputting the plural sets of forward projection data for the respective substances based on the X-ray CT image I2 into the trained model M1, the image processing function 342 acquires raw data R3. In the case illustrated in FIG. 3, the raw data R3 correspond to the optional spectral information, "135 kVp".

For example, the trained model M1 has learnt the coefficients, "c1", "c2", and "c3", expressed in Equation (1). These coefficients are regarded as coefficients of path lengths and dependence of these coefficients on X-ray energy (kVp) is low. Therefore, in a case where optional spectral information is input, the learnt coefficients, "c1", "c2", and "c3", are also used to enable the raw data R3 to be generated from the plural sets of forward projection data. That is, the trained model M1 enables a conversion process to other X-ray energy (kVp).

Furthermore, on the basis of the raw data R3 corresponding to the optional spectral information, the image processing function 342 is also able to generate an X-ray CT image corresponding to the optional spectral information. The display control function 343 is able to display the X-ray CT image corresponding to the optional spectral information on the display 32.

The image processing function 342 may perform a substance discrimination process using plural X-ray CT images respectively corresponding to plural pieces of spectral information, the plural X-ray CT images having been acquired using the trained model M1. A case where an X-ray CT image corresponding to high energy and an X-ray CT image corresponding to low energy have been acquired using the trained model M1 will be described hereinafter. For example, the image processing function 342 is able to generate a reference substance image of each of plural reference substances by resolving, according to reference substance, the X-ray CT image corresponding to high energy and the X-ray CT image corresponding to low energy. Furthermore, on the basis of the reference substance images generated, the image processing function 342 is able to generate various images further, such as a monochromatic X-ray image, a density image, and an effective atomic number image.

Figure 5A:
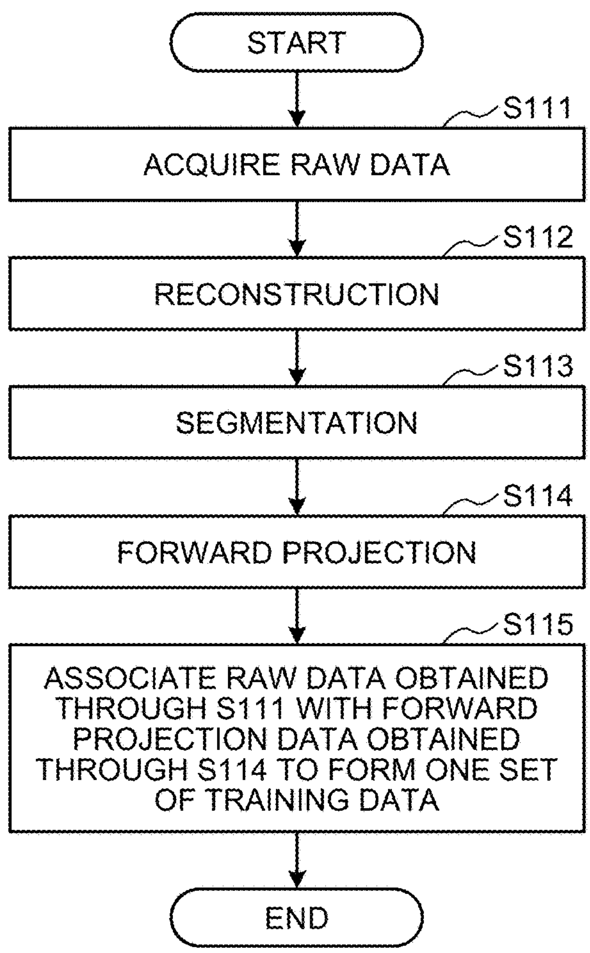
FIG. 5A is a flowchart for explanation of a process at the learning phase by the medical information processing apparatus according to the first embodiment.
Figure 5B:
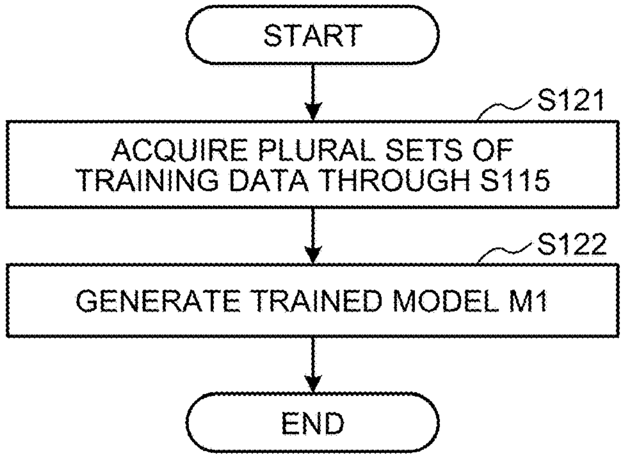
FIG. 5B is a flowchart for explanation of a process at the learning phase by the medical information processing apparatus according to the first embodiment.

A series of processes by the medical information processing apparatus 1 at the learning phase described by reference to FIG. 3 will be described by use of FIG. 5A and FIG. 5B. FIG. 5A and FIG. 5B are flowcharts for explanation of processes at the learning phase by the medical information processing apparatus 1 according to the first embodiment.

Firstly, the acquisition function 111 acquires raw data (Step S111) and reconstructs an X-ray CT image from the raw data (Step S112). The acquisition function 111 may acquire an X-ray CT image reconstructed at another device, instead of implementing Step S111 and Step S112. Subsequently, the acquisition function 111 performs segmentation of the acquired X-ray CT image according to substance, and acquires sets of distribution data on substances (Step S113). Subsequently, the acquisition function 111 performs a forward projection process for each of the sets of distribution data on the substances and acquires plural sets of forward projection data for the respective substances (Step S114). The acquisition function 111 then associates the raw data acquired through Step S111, with the plural sets of forward projection data acquired through Step S114, and stores the associated data as one set of training data into the memory 12 (Step S115). For example, the acquisition function 111 associates the raw data R1 and the plural sets of forward projection data (the forward projection data P11, forward projection data P12, and forward projection data P13) illustrated in FIG. 3 with each other and stores the associated data as one set of training data into the memory 12.

The acquisition function 111 executes the series of steps illustrated in FIG. 5A every time new raw data are acquired. The training data acquired through Step S115 are thereby accumulated in the memory 12. The learning function 112 acquires plural sets of the training data acquired through Step S115 from the memory 12 (Step S121), executes machine learning using the plural sets of training data, and thereby generates the trained model M1 (Step S122).

Figure 6:
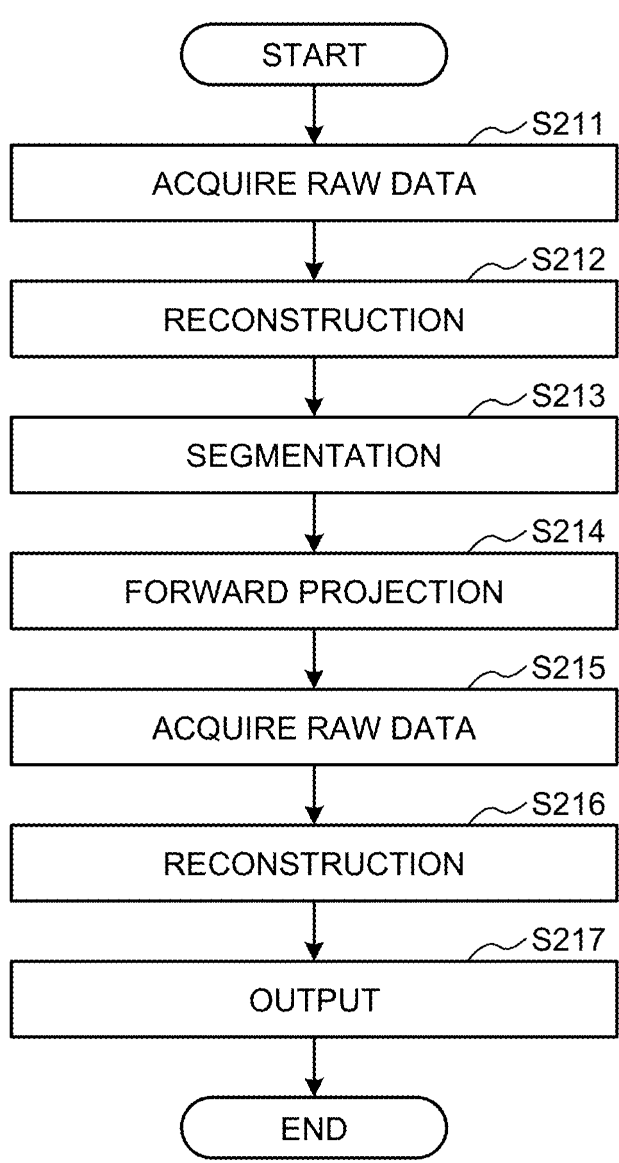
FIG. 6 is a flowchart for explanation of a process at the application phase by the medical information processing apparatus according to the first embodiment.

A series of processes by the medical information processing apparatus 3 at the application phase described by reference to FIG. 4 will be described next by use of FIG. 6. FIG. 6 is a flowchart for explanation of a process at the application phase by the medical information processing apparatus 3 according to the first embodiment.

Firstly, the acquisition function 341 acquires raw data (Step S211) and reconstructs an X-ray CT image from the raw data (Step S212). For example, at Step S212, the acquisition function 341 reconstructs the X-ray CT image I2 from the raw data R2 illustrated in FIG. 4. The acquisition function 341 may acquire the X-ray CT image I2 reconstructed at another device, instead of implementing Step S211 and Step S212. The X-ray CT image I2 is an example of a first CT image of a subject, the first CT image being acquired by a CT scan corresponding to first spectral information.

Subsequently, the acquisition function 341 performs segmentation of the acquired X-ray CT image (the first CT image, such as the X-ray CT image I2) according to substance and acquires sets of distribution data on substances (Step S213). That is, by applying a computer segmentation process to the first CT image, the acquisition function 341 acquires sets of distribution data on plural substances.

Subsequently, the image processing function 342 performs, on the basis of optional spectral information and the attenuation coefficients for the substances, a forward projection process for each of the sets of distribution data on the substances, and acquires plural sets of forward projection data for the respective substances (Step S214). For example, as illustrated in FIG. 4, on the basis of optional spectral information, "135 kVp", the image processing function 342 performs a forward projection process for the distribution data D21 to acquire the forward projection data P21, performs a forward projection process for the distribution data D22 to acquire the forward projection data P22, and performs a forward projection process for the distribution data D23 to acquire the forward projection data P23. That is, by performing a forward projection process based on second spectral information for each of sets of distribution data on plural substances, the image processing function 342 is able to acquire plural sets of forward projection data.

By inputting the plural sets of forward projection data acquired through Step S214 into the trained model M1, the image processing function 342 acquires raw data corresponding to the optional spectral information (Step S215). For example, as illustrated in FIG. 4, by inputting the forward projection data P21, the forward projection data P22, and the forward projection data P23 into the trained model M1, the image processing function 342 acquires the raw data R3 corresponding to the optional spectral information, "135 kVp". That is, by applying the trained model M1 to the plural sets of forward projection data, the image processing function 342 is able to acquire raw data corresponding to the second spectral information.

Furthermore, the image processing function 342 generates an X-ray CT image corresponding to the optional spectral information, from the raw data corresponding to the optional spectral information, the raw data having been acquired at Step S215 (Step S216). That is, on the basis of the raw data acquired at Step S215, the image processing function 342 reconstructs a second CT image corresponding to the second spectral information. The X-ray CT image corresponding to the optional spectral information is output for display or analysis and provided for use by a user (Step S217). For example, the display control function 343 displays the X-ray CT image corresponding to the optional spectral information, on the display 32. Furthermore, for example, the X-ray CT image corresponding to the optional spectral information is transmitted to any display device (not illustrated in the drawings) via the network NW and displayed at the display device. Furthermore, for example, an analysis result based on the X-ray CT image corresponding to the optional spectral information is displayed on the display 32 or at any display device. Examples of such an analysis result include a reference substance image, a monochromatic X-ray image, a density image, and an effective atomic number image, mentioned above.

A conversion process based on sets of distribution data on plural substances is executed by the processing at Steps S213 to S216 in FIG. 6. For example, in the example of FIG. 4, a conversion process based on the distribution data D21, distribution data D22, and distribution data D23 corresponding to "120 kVp" is executed, the raw data R3 corresponding to "135 kVp" are generated, and the X-ray CT image corresponding to "135 kVp" is further reconstructed on the basis of the distribution data D21. That is, the medical information processing apparatus 3 is able to acquire a second CT image corresponding to second spectral information by: acquiring a first CT image of a subject, the first CT image being acquired by a CT scan corresponding to first spectral information; acquiring sets of distribution data on plural substances by applying a computer segmentation process to the first CT image; and performing a conversion process on the basis of the sets of distribution data on the plural substances.

The trained model M1 described above may be generated for each of various conditions. For example, a trained model M1 may be generated for each of conditions, such as regions to be captured in the X-ray CT image I1 and/or pieces of patient information including ages and physical sizes. For example, the acquisition function 111 may generate plural trained models M1 including a trained model M1 trained using images of "heads", a trained model M1 trained using images of "chests", and a trained model M1 trained using images of "abdomens". In this case, the image processing function 342 uses the trained model M1 acquired according to region to be captured in the X-ray CT image I2 and acquires the raw data R3 corresponding to optional spectral information. The trained model M1 is thereby able to perform a conversion process to other X-ray energy (kVp) more accurately in consideration of influence, such as the region to be captured and/or patient information.

Or, in the above described process of generating the trained model M1, information, such as the region to be captured or patient information, may be additionally used as training data. In this case, the image processing function 342 inputs, in addition to the above described plural sets of forward projection data based on the X-ray CT image I2, information, such as the region to be captured or patient information, to the trained model M1. The trained model M1 is thereby able to perform a conversion process to other X-ray energy value (kVp) more accurately in consideration of influence, such as the region to be captured and/or patient information.

An example of the display at Step S217 will be described next by use of FIG. 7. The display at Step S217 may be performed at another display device different from the medical information processing apparatus 3, but in the example described by reference to FIG. 7, the display control function 343 displays an image on the display 32. Furthermore, without being limited to an X-ray CT image, the image displayed on the display 32 may be an analysis result based on the X-ray CT image (for example, a reference substance image, a monochromatic X-ray image, a density image, or an effective atomic number image), but in the example described by reference to FIG. 7, an X-ray CT image is displayed.

For example, according to the flowchart in FIG. 6, a first CT image corresponding to first spectral information reconstructed at Step S212 and a second CT image corresponding to second spectral information reconstructed at Step S216 are acquired, and the display control function 343 is capable of displaying the first CT image and the second CT image on the display 32. Furthermore, in a case where there are CT images (hereinafter, referred to as past images) collected in the past for the same subject, the display control function 343 may display, in addition to the first CT image and second CT image, the past images on the display 32.

Figure 7:
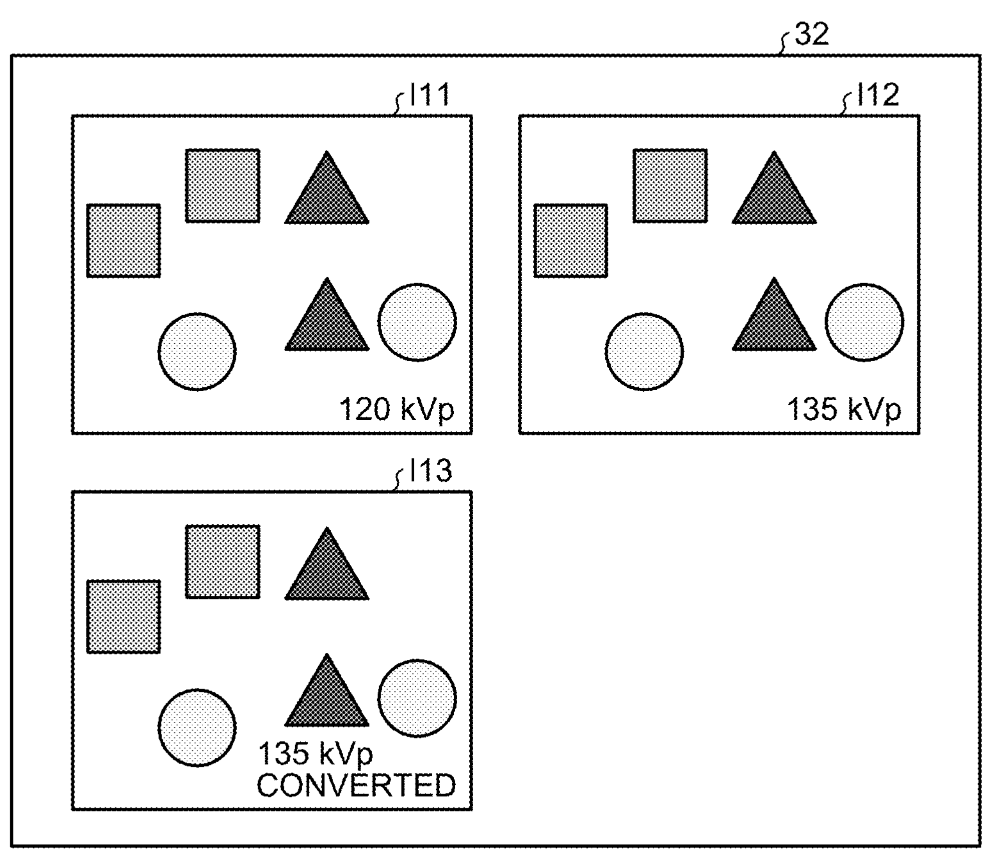
FIG. 7 is an example of display according to the first embodiment.

FIG. 7 illustrates a CT image I11 as an example of the first CT image, a CT image I12 as an example of the past images, and a CT image I13 as an example of the second CT image. The specific form of display, such as the layout and the user interface (UI), may be modified as appropriate. For example, in FIG. 7, three display areas are provided and the CT image I11, the CT image I12, and the CT image I13 are lined up to be displayed in these display areas, but the CT image I11, the CT image I12, and the CT image I13 may be displayed to be able to be switched over to each other in one display area, for example.

The CT image I11 and the CT image I12 are CT images collected from the same subject at different times and dates. For example, in a case where a subject who has suffered an external injury of the whole body is to be examined, a CT scan over an extensive range may be executed and a CT scan over a small range including a damaged region may be executed again thereafter. Furthermore, a CT scan of a range including a lesion may be repeatedly executed for evaluation of progression of the lesion or the treatment effect in treatment planning or follow-up after treatment. In a case where a CT scan is thus executed a plural number of times for the same subject, the display control function 343 is able to acquire, in addition to the CT image I11 that is the first CT image, the CT image I12 that is a past image, and display them on the display 32.

The CT image I13 is a CT image corresponding to "135 kVp" generated by a conversion process based on the CT image I11 corresponding to "120 kVp". The display control function 343 may display a CT image that has not undergone a conversion process, like the CT image I11 or the CT image I12, and a CT image acquired by a conversion process, like the CT image I13, distinguishably from each other. For example, as illustrated in FIG. 7, the display control function 343 may additionally display, "Converted", for the CT image I13 acquired by a conversion process. A user, such as a medical doctor, is thereby able to make a diagnosis while recognizing the CT image I13 as a CT image resulting from a conversion process. For example, the CT image I12 corresponding to the same X-ray energy as the CT image I13 is being displayed in FIG. 7, and the medical doctor is able to make a diagnosis in consideration of the CT image I13 that is the latest image but has undergone a conversion process, as well as the CT image I12 that is a past image but has not undergone a conversion process.

FIG. 4 illustrates the single trained model M1 (the neural network NN) but a conversion process may be performed using plural trained models M1.

For example, the medical information processing apparatus 1 generates a trained model M1 for each substance. For example, the medical information processing apparatus 1 generates each of a trained model M1 corresponding to the attenuation coefficient μ1, a trained model M1 corresponding to the attenuation coefficient μ2, and a trained model M1 corresponding to the attenuation coefficient μ3. In a conversion process in this case, plural sets of forward projection data are acquired by performing a forward projection process based on second spectral information for each of sets of distribution data on plural substances; processed plural sets of forward projection data are acquired by applying the trained models to the plural sets of forward projection data; combined forward projection data are acquired by combining the processed plural sets of forward projection data; and a second CT image is able to be reconstructed on the basis of the combined forward projection data.

For example, by performing a forward projection process based on second spectral information for each of the sets of distribution data D21 to D23 illustrated in FIG. 4, the image processing function 342 acquires the plural sets of forward projection data P21 to P23. Subsequently, by applying the trained model M1 corresponding to the attenuation coefficient μ1 to the forward projection data P21, the image processing function 342 acquires the processed forward projection data P21. Furthermore, by applying the trained model M1 corresponding to the attenuation coefficient μ2 to the forward projection data P22, the image processing function 342 acquires the processed forward projection data P22. By applying the trained model M1 corresponding to the attenuation coefficient μ3 to the forward projection data P23, the image processing function 342 also acquires the processed forward projection data P23. Subsequently, by combining the processed forward projection data P21, the processed forward projection data P22, and the processed forward projection data P23 together, the image processing function 342 acquires the combined forward projection data. The image processing function 342 then reconstructs the second CT image on the basis of the combined forward projection data.

Second Embodiment

In a case described with respect to a second embodiment, a trained model M1 is generated according to X-ray energy (kVp) of an X-ray CT image I1.

For example, as illustrated in FIG. 3, the acquisition function 111 acquires the X-ray CT image I1 captured at "120 kVp" and acquires plural sets of forward projection data on respective substances. The learning function 112 then generates a trained model M1 corresponding to "120 kVp" by machine learning based on the plural sets of forward projection data and the raw data R1 used in generation of the X-ray CT image I1.

Furthermore, the acquisition function 111 acquires an X-ray CT image I1 captured at "100 kVp" and acquires plural sets of forward projection data for respective substances. The learning function 112 then generates a trained model M1 corresponding to "100 kVp" by machine learning based on the plural sets of forward projection data and the raw data R1 used in generation of the X-ray CT image I1. Similarly, the learning function 112 generates trained models M1 respectively corresponding to various X-ray energy values.

After an X-ray CT image I2 is acquired, the image processing function 342 acquires raw data R3 corresponding to optional spectral information, by using a trained model M1 acquired according to spectral information on imaging of the X-ray CT image I2. For example, in a case where the X-ray CT image I2 has been captured at "120 kVp", the image processing function 342 acquires the raw data R3 using the trained model M1 corresponding to "120 kVp".

There may be a case where influence of X-ray energy is nonnegligible even though dependence of the coefficients, "c1", "c2", and "c3" that are learnt by the trained model M1 on X-ray energy (kVp) is low, as described above. In this case, generating trained models M1 respectively corresponding to various X-ray energy values enables reduction of the influence of X-ray energy used in imaging and accurate execution of a conversion process to other X-ray energy (kVp).

Instead of generating trained models M1 respectively corresponding to various X-ray energy values, X-ray energy used in imaging of the X-ray CT image I1 may be used additionally as training data. In this case, the image processing function 342 further inputs, in addition to the above described plural sets of forward projection data based on the X-ray CT image I2, X-ray energy used in imaging of the X-ray CT image I2, into the trained model M1. The trained model M1 is thereby able to perform a conversion process to other X-ray energy (kVp) more accurately in consideration of influence of X-ray energy used in imaging.

Third Embodiment

In the example described above with respect to the first embodiment, the trained model M1 that receives input of plural sets of forward projection data for respective substances and outputs raw data implements acquisition of an X-ray CT image (a second CT image) corresponding to spectral information on X-rays, the spectral information being different from that on X-rays used at the time of imaging. By contrast, in an example described with respect to a third embodiment, trained models M2 that receive input of a CT image and output sets of distribution data for respective substances implement acquisition of a second CT image. In other words, in the example described with respect to the third embodiment, the trained models M2 that execute a computer segmentation process implement acquisition of the second CT image. Components different from those of the above described embodiments will be described hereinafter, and the same reference signs will be assigned to components that are the same as those of the above described embodiments and description thereof will be omitted.

Figure 8:
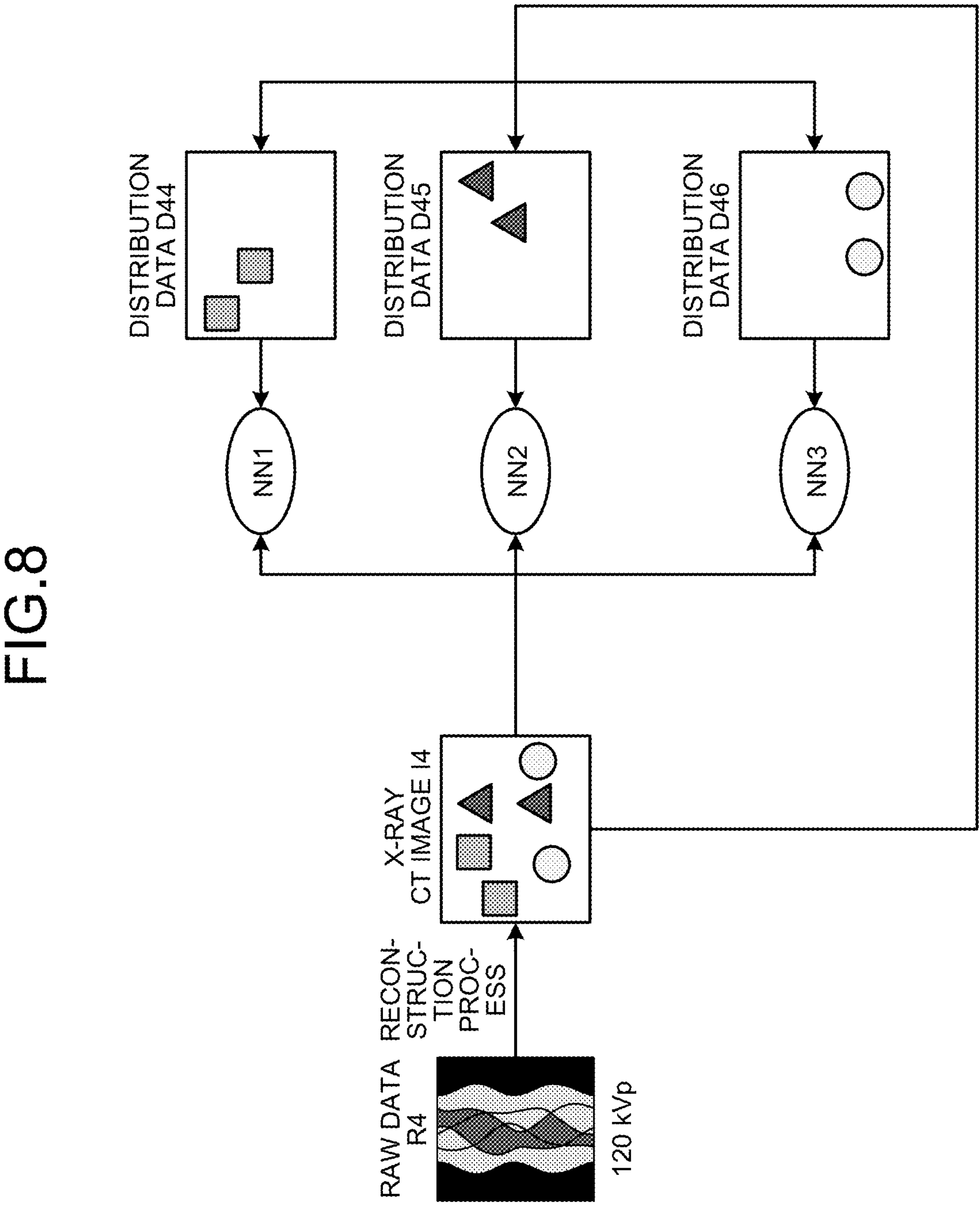
FIG. 8 is a diagram for explanation of a learning phase according to a third embodiment.

A process in which the trained models M2 are generated by the medical information processing apparatus 1 will be described by use of FIG. 8. FIG. 8 is a diagram for explanation of a learning phase according to the third embodiment.

Firstly, imaging of any subject is executed and raw data R4 are collected. Subsequently, a reconstruction process based on the raw data R4 is executed and an X-ray CT image I4 is generated. The acquisition function 111 acquires the X-ray CT image I4. The reconstruction process for the X-ray CT image I4 may be performed by the acquisition function 111 or may be performed at another device.

Subsequently, the acquisition function 111 performs segmentation of the acquired X-ray CT image I4 according to substance and acquires sets of distribution data on substances in the X-ray CT image I4. For example, the acquisition function 111 performs segmentation of the X-ray CT image I4 into different organs. For example, in FIG. 8, the acquisition function 111 performs segmentation of the X-ray CT image I4 according to substance and acquires distribution data D44, distribution data D45, and distribution data D46.

The acquisition function 111 performs the segmentation of the X-ray CT image I4 accurately by a manual or semi-manual method. For example, the acquisition function 111 causes the X-ray CT image I4 to be displayed, receives an input operation from a user, such as a medical doctor, who has referred to the X-ray CT image I4, and thereby acquires the sets of distribution data on the substances in the X-ray CT image I4. Furthermore, for example, the acquisition function 111 performs segmentation of the X-ray CT image I4 by any method, such as Otsu's Binarization Method based on CT values, a region growing method, the snakes method, the graph cuts method, or the mean shift method, and thereafter presents a result of the segmentation to the user. By receiving correction of the result of the segmentation from the user, the acquisition function 111 acquires sets of distribution data on the substances in the X-ray CT image I4.

Subsequently, by executing machine learning using training data including combinations of the X-ray CT image I4 and the distribution data D44, distribution data D45, and distribution data D46, the learning function 112 generates trained models M2.

FIG. 8 illustrates a neural network NN1, a neural network NN2, and a neural network NN3, as an example of the trained models M2. These plural trained models M2 are generated respectively for the substances. Specifically, by executing machine learning using training data including a combination of the X-ray CT image I4 and the distribution data D44 resulting from segmentation of the X-ray CT image I4 for the substance corresponding to the attenuation coefficient $\mu 1$, the learning function 112 generates the neural network NN1. Furthermore, by executing machine learning using training data including a combination of the X-ray CT image I4 and the distribution data D45 resulting from segmentation of the X-ray CT image I4 for the substance corresponding to the attenuation coefficient $\mu 2$, the learning function 112 generates the neural network NN2. By executing machine learning using training data including a combination of the X-ray CT image I4 and the distribution data D46 resulting from segmentation of the X-ray CT image I4 for the substance corresponding to the attenuation coefficient $\mu 3$, the learning function 112 generates the neural network NN3.

An application phase of the trained models M2 will be described next by use of FIG. 9. Firstly, imaging of any subject is executed and raw data R5 are collected. The raw data R5 may be collected from the same subject as the raw data R4 or may be collected from another subject. Furthermore, the raw data R5 may be collected by the X-ray CT apparatus 2 illustrated in FIG. 2 or may be collected by another X-ray CT apparatus. Subsequently, a reconstruction process based on the raw data R5 is executed and an X-ray CT image I5 is generated. The acquisition function 341 acquires the X-ray CT image I5. The reconstruction of the X-ray CT image I5 may be performed by the acquisition function 341 or may be performed at another device.

Subsequently, using the trained models M2, the acquisition function 341 performs segmentation of the acquired X-ray CT image I5 according to substance, and acquires sets distribution data on substances in the X-ray CT image I5. For example, by inputting the X-ray CT image I5 into the neural network NN1, the acquisition function 341 acquires distribution data D51 on the substance corresponding to the attenuation coefficient $\mu 1$. Furthermore, by inputting the X-ray CT image I5 into the neural network NN2, the acquisition function 341 acquires distribution data D52 on the substance corresponding to the attenuation coefficient $\mu 2$. By inputting the X-ray CT image I5 into the neural network NN3, the acquisition function 341 acquires distribution data D53 on the substance corresponding to the attenuation coefficient $\mu 3$.

Subsequently, on the basis of optional spectral information and the attenuation coefficient for each substance, the image processing function 342 performs a forward projection process for each set of distribution data, and acquires plural sets of forward projection data for the respective substances. For example, in the case illustrated in FIG. 9, the image processing function 342 performs a forward projection process for the distribution data D51 to acquire forward projection data P51, performs a forward projection process for the distribution data D52 to acquire forward projection data P52, and performs a forward projection process for the distribution data D53 to acquire forward projection data P53.

This optional spectral information may be different from the spectral information on the imaging of the X-ray CT image I5. For example, in FIG. 9, the X-ray CT image I5 has been captured using X-rays of "120 kVp". By contrast, the optional spectral information set for acquisition of the forward projection data is "135 kVp". By combining the plural sets of forward projection data for the respective substances, the image processing function 342 acquires raw data R6. In the case illustrated in FIG. 9, the raw data R6 correspond to the optional spectral information, "135 kVp".

In FIG. 9, the sets of forward projection data corresponding to the optional spectral information, "135 kVp" are acquired from the sets of distribution data corresponding to the spectral information, "120 kVp", on the imaging. One may consider performing a forward projection process for the X-ray CT image I5 that has not been subjected to segmentation and acquiring raw data corresponding to "135 kVp". However, in this case, the calculation becomes complicated because the forward projection process is performed for the X-ray CT image I5 including a mix of various substances.

By contrast, in the example of FIG. 9, the forward projection process is performed after the segmentation according to substance and the calculation is thereby able to be simplified and accuracy of the conversion process to other X-ray energy (kVp) is thereby able to be improved. In addition, accurately performing the segmentation using the trained models M2 as illustrated in FIG. 9 enables further improvement in the accuracy of the conversion process with a reliable premise that the sets of distribution data resulting from the segmentation are each for a single substance.

Figure 10A:
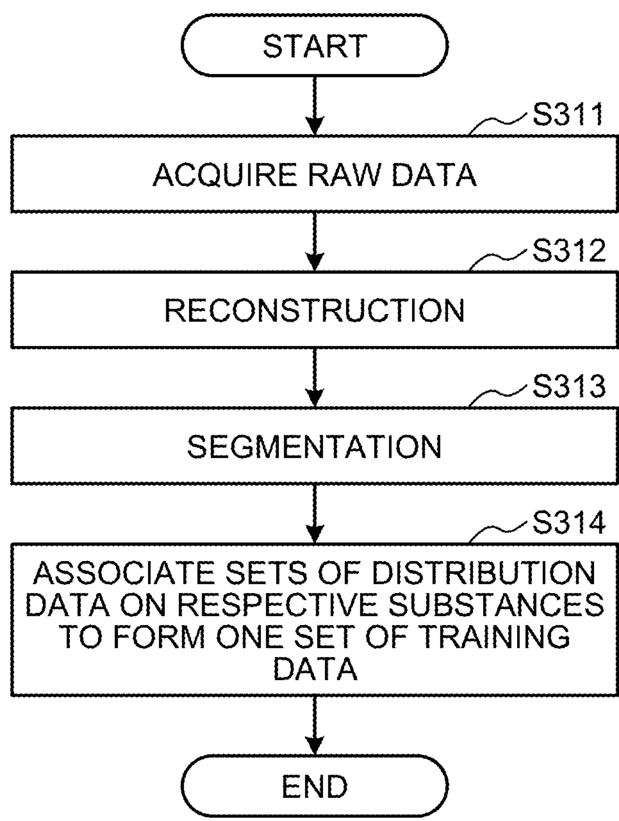
FIG. 10A is a flowchart for explanation of a process at the learning phase by a medical information processing apparatus according to the third embodiment.
Figure 10B:
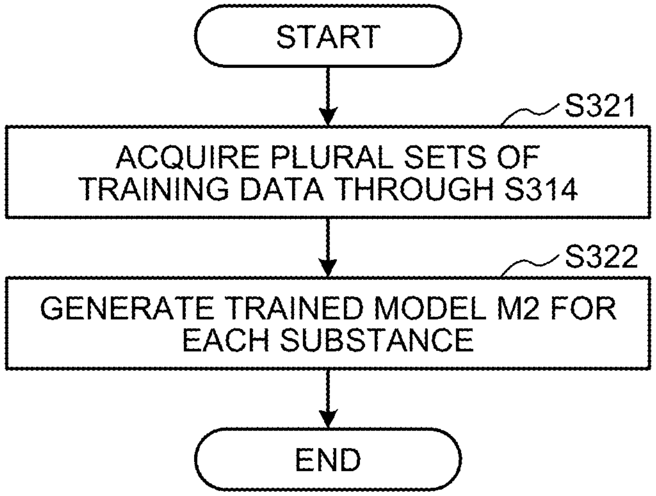
FIG. 10B is a flowchart for explanation of a process at the learning phase by the medical information processing apparatus according to the third embodiment.

A series of processes by the medical information processing apparatus 1 at the learning phase described by reference to FIG. 8 will be described next by use of FIG. 10A and FIG. 10B. FIG. 10A and FIG. 10B are each a flowchart for explanation of a process at the learning phase by the medical information processing apparatus 1 according to the third embodiment.

Firstly, the acquisition function 111 acquires raw data (Step S311) and reconstructs an X-ray CT image from the raw data (Step S312). The acquisition function 111 may acquire an X-ray CT image reconstructed at another device, instead of implementing Step S311 and Step S312. Subsequently, the acquisition function 111 performs segmentation of the acquired X-ray CT image according to substance and acquires sets of distribution data on respective substances (Step S313). The acquisition function 111 performs the segmentation of the X-ray CT image accurately by a manual or semi-manual method. The acquisition function 111 then associates the X-ray CT image acquired through Step S312 with the sets of distribution data for the respective substances acquired through Step S313 and stores the associated X-ray CT image and sets of distribution data as one set of training data into the memory 12 (Step S314).

The acquisition function 111 executes the series of steps illustrated in FIG. 10A every time new raw data are acquired. The training data acquired through Step S314 are thereby accumulated in the memory 12. The learning function 112 acquires plural sets of the training data acquired through Step S314 from the memory 12 (Step S321), executes machine learning using the plural sets of training data, and thereby generates the trained models M2 for the respective substances (Step S322).

A series of processes by the medical information processing apparatus 3 at the application phase described by reference to FIG. 9 will be described next. The flowchart for the application phase according to the third embodiment is similar to that for the application phase according to the first embodiment. The application phase according to the third embodiment will thus be described by use of FIG. 6.

Firstly, the acquisition function 341 acquires raw data (Step S211) and reconstructs an X-ray CT image from the raw data (Step S212). For example, at Step S212, the acquisition function 341 reconstructs the X-ray CT image I2 from the raw data R2 illustrated in FIG. 4. The acquisition function 341 may acquire the X-ray CT image I2 reconstructed at another device, instead of implementing Step S211 and Step S212.

Subsequently, the acquisition function 341 performs segmentation of the acquired X-ray CT image according to substance and acquires sets of distribution data on substances (Step S213). That is, by applying a computer segmentation process to a first CT image, the acquisition function 341 acquires sets of distribution data on plural substances. The acquisition function 341 executes this computer segmentation process on the basis of the trained models M2 acquired by machine learning. In other words, in the computer segmentation process according to the third embodiment, plural sets of distribution data on plural substances are acquired from the first CT image on the basis of the trained models M2.

Subsequently, the image processing function 342 performs, on the basis of optional spectral information and attenuation coefficients for the respective substances, a forward projection process for each of the sets of distribution data on the substances, and acquires plural sets of forward projection data for the respective substances (Step S214). For example, as illustrated in FIG. 9, on the basis of optional spectral information, "135 kVp", the image processing function 342 performs a forward projection process for the distribution data D51 to acquire the forward projection data P51, performs a forward projection process for the distribution data D52 to acquire the forward projection data P52, and performs a forward projection process for the distribution data D53 to acquire the forward projection data P53.

By combining the plural sets of forward projection data acquired through Step S214, the image processing function 342 acquires raw data corresponding to the optional spectral information (Step S215). For example, as illustrated in FIG. 9, the image processing function 342 acquires the raw data R6 corresponding to the optional spectral information, "135 kVp", by combining the forward projection data P51, the forward projection data P52, and the forward projection data P53.

Furthermore, the image processing function 342 generates an X-ray CT image corresponding to the optional spectral information, from the raw data corresponding to the optional spectral information, the raw data having been acquired at Step S215 (Step S216). The X-ray CT image corresponding to the optional spectral information is output for display or analysis and provided for use by a user (Step S217).

Similarly to the case of the trained model M1, the trained models M2 may be generated for each of various conditions, such as regions to be captured and/or patient information, or information, such as regions to be captured and/or patient information, may be used additionally as training data in the process of generating the trained models M2. Furthermore, the above described second embodiment may be implemented by being combined with this third embodiment. That is, the trained models M2 may be generated for each X-ray energy value (kVp) or X-ray energy may be used additionally as training data in the process of generating the trained models M2.

Fourth Embodiment

In an example described with respect to a fourth embodiment, input of sets of distribution data on respective substances is received and an X-ray CT image (a second CT image) corresponding to spectral information on X-rays is acquired by trained models M3 that output distribution data corresponding to optional spectral information, the spectral information being different from that on X-rays used at the time of imaging. Components different from those of the above described embodiments will be described hereinafter, and the same reference signs will be assigned to components that are the same as those of the above described embodiments and description thereof will be omitted.

Figure 11:
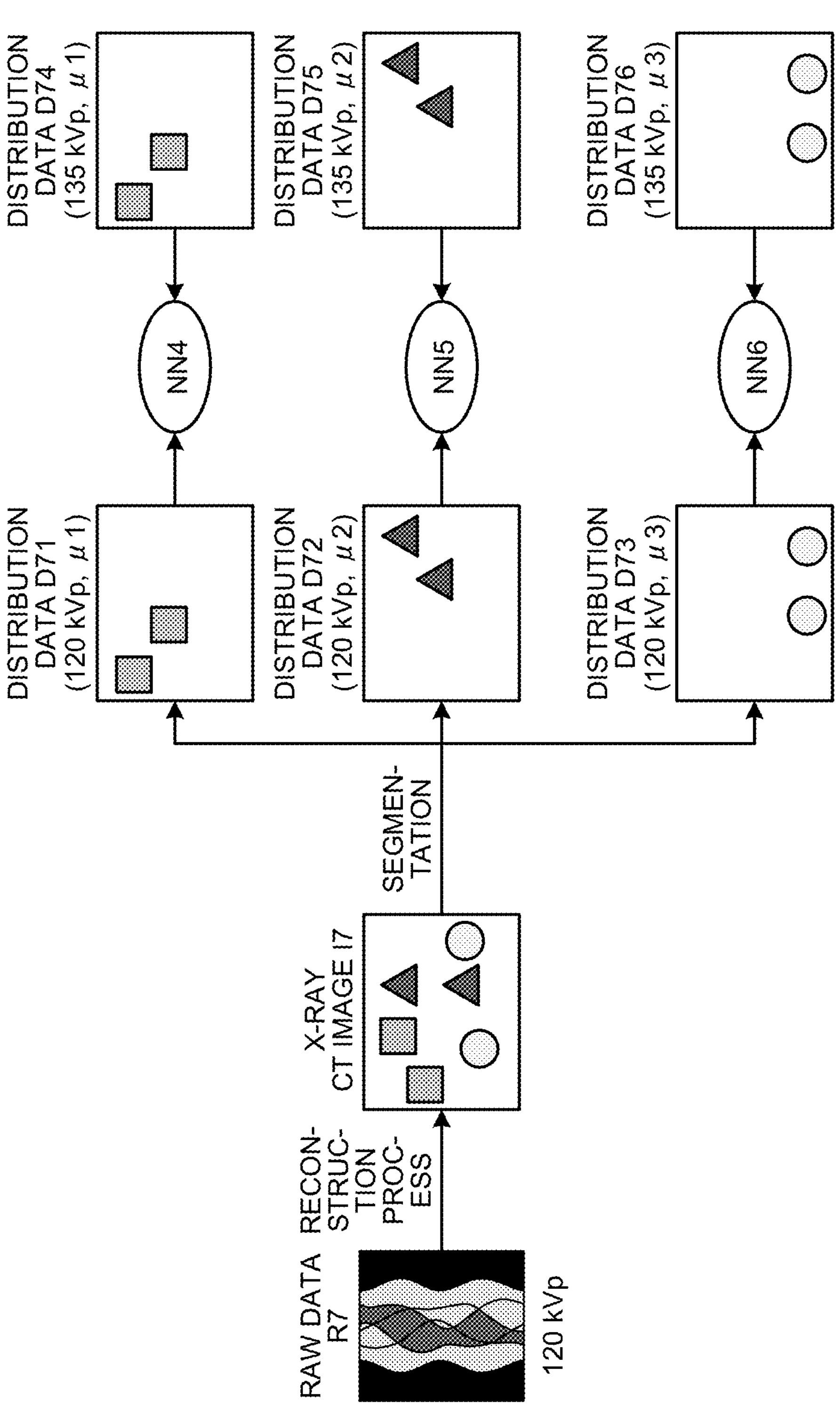
FIG. 11 is a diagram for explanation of a learning phase according to a fourth embodiment.

A process in which the trained models M3 are generated by the medical information processing apparatus 1 will be described by use of FIG. 11. FIG. 11 is a diagram for explanation of a learning phase according to the fourth embodiment.

Firstly, imaging of any subject is executed and raw data R7 are collected. Subsequently, a reconstruction process based on the raw data R7 is executed and an X-ray CT image I7 is generated. The acquisition function 111 acquires the X-ray CT image I7. The reconstruction process for the X-ray CT image I7 may be performed by the acquisition function 111 or may be performed at another device.

Subsequently, the acquisition function 111 performs segmentation of the acquired X-ray CT image I7 according to substance and acquires sets of distribution data on substances in the X-ray CT image I7. For example, in FIG. 11, the acquisition function 111 performs segmentation of the X-ray CT image I7 according to substance and acquires distribution data D71, distribution data D72, and distribution data D73. The acquisition function 111 may perform this segmentation by a manual or semi-manual method, or may automatically perform segmentation by a method, such as Otsu's Binarization Method based on CT values.

In FIG. 11, the sets of distribution data D71 to D73 correspond to X-ray energy, "120 kVp", used at the time of imaging. The learning function 112 generates the trained models M3 by executing machine learning using training data including combinations of the sets of distribution data D71 to D73 and sets of distribution data D74 to D76 corresponding to X-ray energy, "135 kVp", different from that for the sets of distribution data D71 to D73.

FIG. 11 illustrates neural networks NN4 to NN6 as an example of the trained models M3. In the case illustrated in FIG. 11, the neural network NN4 has a function of receiving input of a set of distribution data on the substance corresponding to the attenuation coefficient $\mu 1$, the set of distribution data corresponding to the X-ray energy, "120 kVp", and outputting a set of distribution data on the substance, the set of distribution data corresponding to the X-ray energy, "135 kVp". Furthermore, the neural network NN5 has a function of receiving input of a set of distribution data on the substance corresponding to the attenuation coefficient $\mu 2$, the set of distribution data corresponding to the X-ray energy, "120 kVp", and outputting a set of distribution data on the substance, the set of distribution data corresponding to the X-ray energy, "135 kVp". The neural network NN6 has a function of receiving input of a set of distribution data on the substance corresponding to the attenuation coefficient μ3, the set of distribution data corresponding to the X-ray energy, "120 kVp", and outputting a set of distribution data on the substance, the set of distribution data corresponding to the X-ray energy, "135 kVp".

The sets of distribution data D74 to D76 are able to be acquired by, for example, segmentation of an X-ray CT image collected by a CT scan corresponding to the X-ray energy, "135 kVp", from the same subject as the X-ray CT image I7 in FIG. 11.

Another method of acquiring the sets of distribution data D74 to D76 will be described by use of FIG. 12. FIG. 12 is a diagram illustrating an example of a method of acquiring training data according to the fourth embodiment. Firstly, as described with respect to FIG. 11, the acquisition function 111 performs segmentation of the X-ray CT image I7 according to substance and acquires the sets of distribution data D71 to D73 corresponding to the X-ray energy, "120 kVp", used at the time of imaging.

Subsequently, on the basis of spectral information different from that on the imaging, the acquisition function 111 performs forward projection processes and acquires the sets of forward projection data P71 to P73. For example, in FIG. 12, on the basis of spectral information, "135 kVp", different from that on the imaging, the acquisition function 111 performs a forward projection process for the set of distribution data D71 to acquire the set of forward projection data P71, performs a forward projection process for the set of distribution data D72 to acquire the set of forward projection data P72, and performs a forward projection process for the set of distribution data D73 to acquire the set of forward projection data P73.

The acquisition function 111 then performs a reconstruction process for each of the sets of forward projection data P71 to P73 and acquires the sets of distribution data D74 to D76 corresponding to the spectral information, "135 kVp". Specifically, in FIG. 12, the acquisition function 111 reconstructs the set of distribution data D74 on the basis of the forward projection data P71, reconstructs the set of distribution data D75 on the basis of the forward projection data P72, and reconstructs the set of distribution data D76 on the basis of the set of forward projection data P73. The reconstruction method is not particularly limited, and the acquisition function 111 may reconstruct the sets of distribution data D74 to D76 by any method, such as an FBP method, a successive approximation reconstruction method, a successive approximation applied reconstruction method, or a DLR method.

An application phase for the trained models M3 will be described next by use of FIG. 13. Firstly, imaging of any subject is executed and raw data R8 are collected. The raw data R8 may be collected from the same subject as the raw data R7 or may be collected from another subject. Furthermore, the raw data R8 may be collected by the X-ray CT apparatus 2 illustrated in FIG. 2 or may be collected by another X-ray CT apparatus. Subsequently, a reconstruction process based on the raw data R8 is executed and an X-ray CT image I8 is generated. The acquisition function 341 acquires the X-ray CT image I8. The reconstruction of the X-ray CT image I8 may be performed by the acquisition function 341 or may be performed at another device.

Subsequently, the acquisition function 341 performs segmentation of the acquired X-ray CT image I8 according to substance and acquires sets of distribution data on substances in the X-ray CT image I8. For example, the acquisition function 341 performs segmentation of the X-ray CT image I8 according to substance and acquires a set of distribution data D81 on the substance corresponding to the attenuation coefficient μ1, a set of distribution data D82 on the substance corresponding to the attenuation coefficient μ2, and a set of distribution data D83 on the substance corresponding to the attenuation coefficient μ3.

Subsequently, the image processing function 342 acquires sets of distribution data D91 to D93 corresponding to X-ray energy, "135 kVp", different from that used at the time of imaging, by inputting the sets of distribution data D81 to D83 corresponding to X-ray energy, "120 kVp", used at the time of imaging, into the trained models M3. Specifically, the image processing function 342 acquires the set of distribution data D91 by inputting the set of distribution data D81 into the neural network NN4. Furthermore, the image processing function 342 acquires the set of distribution data D92 by inputting the set of distribution data D82 into the neural network NN5. The image processing function 342 acquires the set of distribution data D93 by inputting the set of distribution data D83 into the neural network NN6.

That is, in a conversion process according to the fourth embodiment, applying the trained models M3 respectively to the sets of distribution data D81 to D83 enables the sets of distribution data D91 to D93 to be acquired. The sets of distribution data D91 to D93 are an example of processed distribution data on plural substances corresponding to second spectral information.

Furthermore, by combining the sets of distribution data D91 to D93, the image processing function 342 acquires an X-ray CT image I9 corresponding to the X-ray energy, "135 kVp", different from that used at the time of imaging. That is, combining the processed sets of distribution data on the plural substances enables acquisition of a second CT image corresponding to the second spectral information.

One may consider performing machine learning using training data including pairs of X-ray CT images for different X-ray energy values and directly converting an X-ray CT image corresponding to the X-ray energy, "120 kVp", to an X-ray CT image corresponding to the X-ray energy, "135 kVp". However, in this case, calculation becomes complicated because a conversion process is performed for the X-ray CT image including a mix of various substances. By contrast, in the examples of FIG. 11 to FIG. 13, the learning phase and the application phase are implemented after the segmentation according to substance. The calculation is thereby able to be simplified and the accuracy of the conversion process to other X-ray energy (kVp) is thereby able to be improved.

Figures 14A, 14B:
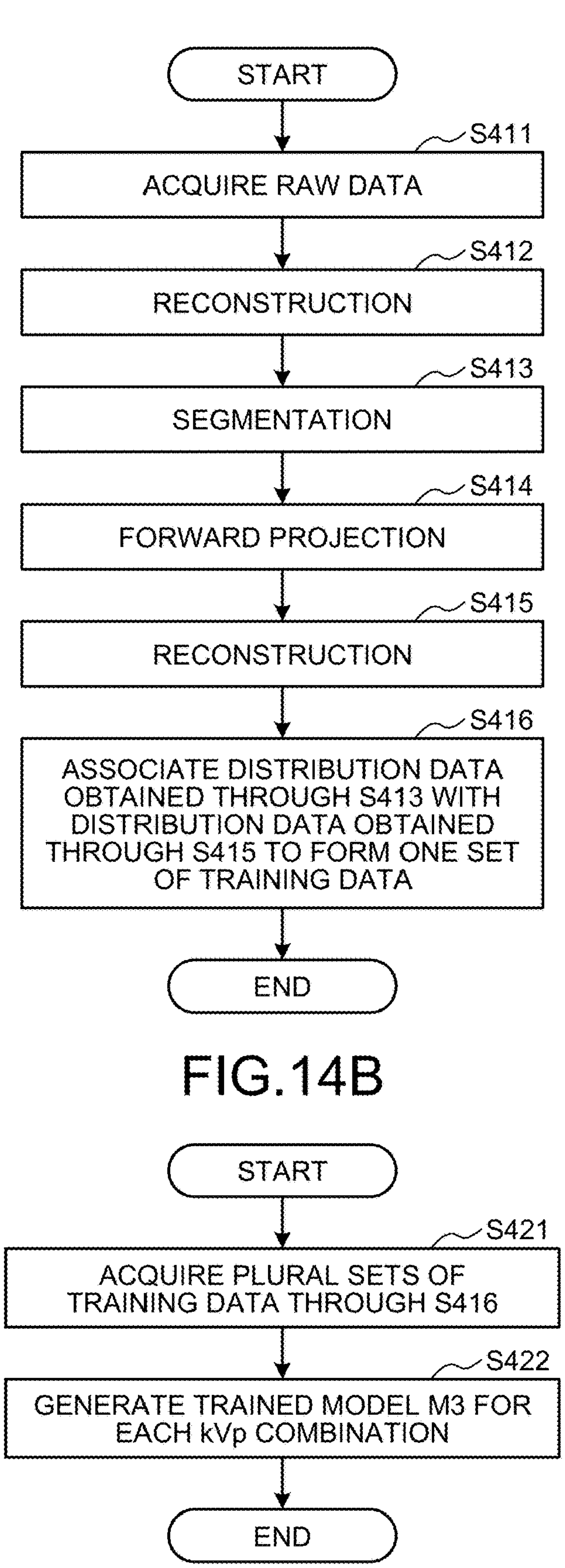
FIG. 14A is a flowchart for explanation of a process at the learning phase by a medical information processing apparatus according to the fourth embodiment.
FIG. 14B is a flowchart for explanation of a process at the learning phase by the medical information processing apparatus according to the fourth embodiment.

A series of processes by the medical information processing apparatus 1 at the learning phase described by reference to FIG. 11 will be described next by use of FIG. 14A and FIG. 14B. FIG. 14A and FIG. 14B are each a flowchart for explanation of a process at the learning phase by the medical information processing apparatus 1 according to the fourth embodiment. Similarly to the case illustrated in FIG. 12, in an example described by reference to FIG. 14A and FIG. 14B, one set of training data is acquired by executing a forward projection process and a reconstruction process with spectral information different from that on imaging.

Firstly, the acquisition function 111 acquires raw data (Step S411) and reconstructs an X-ray CT image from the raw data (Step S412). The acquisition function 111 may acquire an X-ray CT image reconstructed at another device, instead of implementing Step S411 and Step S412. Subsequently, the acquisition function 111 performs segmentation of the acquired X-ray CT image according to substance and acquires sets of distribution data on respective substances (Step S413). Subsequently, for each of the sets of distribution data acquired at Step S413, the acquisition function 111 performs a forward projection process with spectral information different from that on imaging (Step S414) and reconstructs sets of distribution data corresponding to the spectral information different from that on the imaging, from sets of forward projection data acquired (Step S415). The acquisition function 111 associates the sets of distribution data acquired through Step S413 with the sets of distribution data acquired through Step S415 and stores the associated sets of distribution data as one set of training data into the memory 12 (Step S416).

The acquisition function 111 executes the series of steps illustrated in FIG. 14A every time new raw data are acquired. The training data acquired through Step S416 are thereby accumulated in the memory 12. The learning function 112 acquires plural sets of the training data acquired through Step S416 from the memory 12 (Step S421), executes machine learning using the plural sets of training data, and thereby generates the trained models M3 for each X-ray energy (kVp) combination (Step S422).

Figure 15:
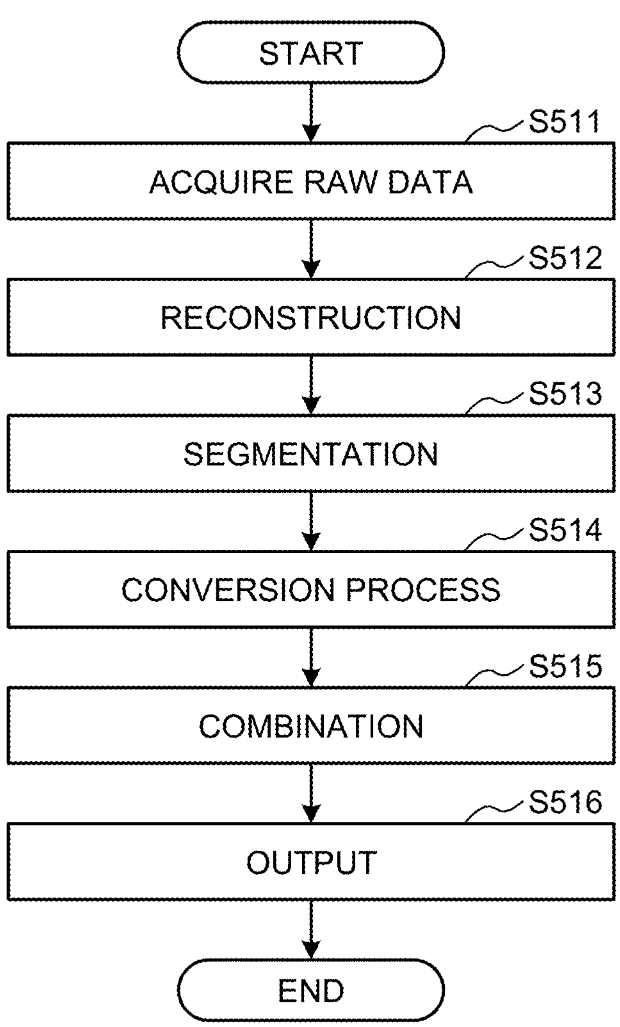
FIG. 15 is a flowchart for explanation of a process at the application phase by the medical information processing apparatus according to the fourth embodiment.

A series of processes by the medical information processing apparatus 3 at the application phase described by reference to FIG. 13 will be described next by use of FIG. 15. FIG. 15 is a flowchart for explanation of a process at the application phase by the medical information processing apparatus 3 according to the fourth embodiment.

Firstly, the acquisition function 341 acquires raw data (Step S511) and reconstructs an X-ray CT image from the raw data (Step S512). For example, at Step S512, the acquisition function 341 reconstructs the X-ray CT image I8 from the raw data R8 illustrated in FIG. 13. The acquisition function 341 may acquire the X-ray CT image I8 reconstructed at another device, instead of implementing Step S511 and Step S512. Subsequently, the acquisition function 341 performs segmentation of the acquired X-ray CT image according to substance and acquires sets of distribution data on substances (Step S513).

Subsequently, the image processing function 342 executes a conversion process for each of the sets of distribution data acquired at Step S513, by using the trained models M3 (Step S514). For example, as illustrated in FIG. 13, the image processing function 342 converts the sets of distribution data D81 to D83 corresponding to the X-ray energy, "120 kVp", into the sets of distribution data D91 to D93 corresponding to the X-ray energy, "135 kVp", using the neural networks NN4 to NN6.

By combining the plural sets of distribution data acquired through Step S514, the image processing function 342 acquires an X-ray CT image corresponding to X-ray energy different from that used at the time of imaging (Step S515). For example, as illustrated in FIG. 13, the image processing function 342 combines the sets of distribution data D91 to D93 and acquires the X-ray CT image I9 corresponding to the X-ray energy, "135 kVp", different from that used at the time of imaging.

Similarly to the case of the trained model M1, the trained models M3 may be generated for each of various conditions, such as regions to be captured and/or patient information, or information, such as regions to be captured and/or patient information, may be used additionally as training data in the process of generating the trained models M3.

OTHER EMBODIMENTS

FIG. 2 illustrates the X-ray CT apparatus 2 and the medical information processing apparatus 3 to be separately bodied but they may be integrated with each other. For example, a console device included in the X-ray CT apparatus 2 may function as the medical information processing apparatus 3 and implement the application phase illustrated in FIG. 4.

Furthermore, according to the description by reference to FIG. 1 and FIG. 2, the medical information processing apparatus 1 implements the learning phase and the medical information processing apparatus 3 implements the application phase, but the learning phase and the application phase may be implemented by the same apparatus. That is, the medical information processing apparatus 3 or the X-ray CT apparatus 2 may implement the learning phase illustrated in FIG. 3.

The term, "processor", used in the above description means, for example: a CPU; a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). In a case where a processor is a CPU, for example, the processor implements its function by reading and executing a program stored in a storage. In contrast, in a case where the processor is, for example, an ASIC, instead of the program being stored in a storage, the function is directly incorporated, as a logic circuit, in circuitry of the processor. Each processor according to the embodiments is not necessarily configured as a single circuit, and plural independent circuits may be combined together to be configured as a single processor for their functions to be implemented. Furthermore, plural components in each drawing may be integrated into a single processor for their functions to be implemented.

It has been described that the single memory 12 stores the programs corresponding to the processing functions of the processing circuitry 11 in FIG. 1. It has also been described that the single memory 31 stores the programs corresponding to the processing functions of the processing circuitry 34 in FIG. 2. However, the embodiments are not limited to these configurations. For example, plural memories 12 may be arranged in a distributed manner and the processing circuitry 11 may be configured to read the corresponding programs from the individual memories 12. Similarly, plural memories 31 may be arranged in a distributed manner and the processing circuitry 34 may be configured to read the corresponding programs from the individual memories 31. Furthermore, instead of being stored in the memory 12 or the memory 31, the programs may be directly incorporated in a circuit of a processor. In this case, by reading and executing the programs incorporated in the circuit, the processor implements the functions.

The components of the apparatuses according to the embodiments described above have been functionally and conceptually illustrated in the drawings and are not necessarily configured physically as illustrated in the drawings. That is, specific forms of distribution and integration of the apparatuses are not limited to those illustrated in the drawings, and all or part of each apparatus may be configured to be distributed or integrated functionally or physically in any units, according to various loads and/or use situations, for example. Furthermore, all or any part of the processing functions executed in the apparatuses may be implemented by a CPU and a program or programs analyzed and executed by the CPU or implemented as hardware by wired logic.

The medical information processing methods described above with respect to the embodiments may each be implemented by a computer, such as a personal computer or a work station, executing a program that has been prepared beforehand. This program may be provided via a network, such as the Internet. Furthermore, this program may be recorded in a computer-readable non-transitory recording medium, such as a hard disk, a flexible disk (FD), a CD-ROM, an MO, or a DVD, and executed by being read by a computer from the recording medium.

At least one of the embodiments described above enables acquisition of an X-ray CT image corresponding to spectral information on X-rays different from spectral information on X-rays used at the time of imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing method, including:

acquiring an X-ray CT image and spectral information on imaging of the X-ray CT image, performing segmentation of the X-ray CT image according to a substance and acquiring distribution data on substances in the X-ray CT image, performing a forward projection process for the distribution data based on the spectral information and an attenuation coefficient for each substance, and acquiring plural sets of forward projection data respectively for the substances; and generating a trained model by machine learning based on the plural sets of forward projection data and raw data used in generation of the X-ray CT image.

2. The medical information processing method according to claim 1, wherein input data that are the plural sets of forward projection data and output data that are the raw data are input to a neural network, and the trained model is generated by causing the neural network to learn to minimize an error between a sum of the plural sets of forward projection data and the raw data.

3. The medical information processing method according to claim 2, further including:

acquiring the trained model, another X-ray CT image different from the X-ray CT image, and spectral information, performing segmentation of the another X-ray CT image according to substance and acquiring distribution data on substances in the another X-ray CT image, performing a forward projection process for the distribution data based on the spectral information and the attenuation coefficient for each substance, and acquiring plural sets of forward projection data respectively for the substances; and acquiring raw data corresponding to the spectral information by inputting the plural sets of forward projection data based on the another X-ray CT image into the trained model.

4. The medical information processing method according to claim 3, wherein the spectral information is set based on an X-ray energy value input by a user.

5. A medical information processing apparatus, comprising:

processing circuitry configured to acquire an X-ray CT image and spectral information on imaging of the X-ray CT image, perform segmentation of the X-ray CT image according to substance and acquires distribution data on substances in the X-ray CT image, perform a forward projection process for the distribution data based on the spectral information and an attenuation coefficient for each substance, and acquire plural sets of forward projection data respectively for the substances; and generate a trained model by machine learning based on the plural sets of forward projection data and raw data used in generation of the X-ray CT image.

6. A medical information processing method, wherein acquiring a first CT image of a subject, the first CT image being acquired by a CT scan corresponding to first spectral information, and acquiring sets of distribution data on plural substances by application of a computer segmentation process to the first CT image, acquiring a second CT image corresponding to second spectral information is by a conversion process based on the sets of distribution data on the plural substances, outputting the second CT image to be displayed or analyzed, and executing any one of the computer segmentation process or the conversion process based on a trained model acquired by machine learning.

7. The medical information processing method according to claim 6, wherein the step of acquiring the sets of distribution data on the plural substances comprises acquiring the sets of distribution data from the first CT image based on the trained model in the computer segmentation process.

8. The medical information processing method according to claim 6, wherein acquiring plural sets of forward projection data by a forward projection process based on the second spectral information for each of the sets of distribution data on the plural substances, acquiring processed plural sets of forward projection data by application of the trained model to the plural sets of forward projection data, acquiring combined forward projection data by a combination of the processed plural sets of forward projection data, and reconstructing the second CT image based on the combined forward projection data.

9. The medical information processing method according to claim 6, further comprising:

acquiring processed sets of distribution data on the plural substances by application of the trained model to each of the sets of distribution data on the plural substances in the conversion process, the processed sets of distribution data corresponding to the second spectral information, and acquiring the second CT image corresponding to the second spectral information by combination of the processed sets of distribution data on the plural substances.

10. The medical information processing method according to claim 6, further comprising:

in the conversion process, acquiring plural sets of forward projection data by a forward projection process based on the second spectral information for each of the sets of distribution data on the plural substances, acquiring raw data corresponding to the second spectral information by application of the trained model to the plural sets of forward projection data, and reconstructing the second CT image based on the raw data.

* * * * *